(12) United States Patent
Takahashi

(10) Patent No.: US 8,900,269 B2
(45) Date of Patent: Dec. 2, 2014

(54) THREAD-FIXING TOOL

(71) Applicant: Olympus Medical Systems Corp., Tokyo (JP)

(72) Inventor: Shinji Takahashi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/974,827

(22) Filed: Aug. 23, 2013

(65) Prior Publication Data
US 2014/0081326 A1 Mar. 20, 2014

Related U.S. Application Data

(63) Continuation of application No. PCT/JP2013/053432, filed on Feb. 13, 2013.

(60) Provisional application No. 61/604,850, filed on Feb. 29, 2012.

(51) Int. Cl.
*A61B 17/04* (2006.01)

(52) U.S. Cl.
CPC ..... *A61B 17/0401* (2013.01); *A61B 2017/0424* (2013.01); *A61B 17/04* (2013.01)
USPC .......................................... 606/232; 606/151

(58) Field of Classification Search
USPC ................ 606/139, 148, 151, 232; 24/115 G, 24/115 H, 115 M, 115 R, 136 R, 453, 24/457–462
See application file for complete search history.

(56) References Cited

U.S. PATENT DOCUMENTS

| 3,976,079 A | * | 8/1976 | Samuels et al. | 606/232 |
| 5,919,208 A | * | 7/1999 | Valenti | 606/232 |
| 7,033,379 B2 | * | 4/2006 | Peterson | 606/232 |

FOREIGN PATENT DOCUMENTS

| JP | A-2001-500778 | 1/2001 |
| JP | A-2009-538215 | 11/2009 |
| JP | A-2012-24276 | 2/2012 |
| WO | WO 99/04698 A1 | 2/1999 |
| WO | WO 2007/140309 A2 | 12/2007 |
| WO | WO 2010/014119 A1 | 2/2010 |

OTHER PUBLICATIONS

International Search Report issued in International Application No. PCT/JP2013/053432 mailed Apr. 2, 2013 (with translation).

* cited by examiner

*Primary Examiner* — Dianne Dornbusch
*Assistant Examiner* — Robert Lynch
(74) *Attorney, Agent, or Firm* — Oliff PLC

(57) ABSTRACT

A thread-fixing tool includes a first member in which a lumen opened at an end surface through which a suture thread is inserted, and a communication path having a first end opened at the end surface and a second end in communication with an intermediate portion of the lumen are formed, and a second member having a shaft portion inserted into the communication path of the first member, and a pressing portion which is formed at a distal portion of the shaft portion and which is capable of deforming outwardly in a radial direction of the shaft portion, wherein the pressing portion is guided to the intermediate portion of the lumen through the communication path, and deformed in a direction crossing an insertion direction of the suture thread to push the suture thread against an inner wall of the lumen.

5 Claims, 25 Drawing Sheets

THREAD-FIXING TOOL

The present application is a Continuation of International Patent Application No. PCT/JP2013/053432, filed Feb. 13, 2013, claiming priority on U.S. Patent Provisional Application No. 61/604,850, filed in United States of America on Feb. 29, 2012, the contents of said U.S. Patent Provisional Application and said PCT Application being incorporated herein.

BACKGROUND OF THE INVENTION

1. Field of the Invention

The present invention relates to a thread-fixing tool configured to fix a medical suture thread.

2. Description of Related Art

In the related art, as a thread-fixing tool configured to fix a medical suture thread used in surgical treatment to the inside of the body or the alimentary canal, a thread-fixing tool having a cylindrical member and a post-shaped member inserted into the cylindrical member is known (for example, see Japanese Unexamined Patent Application First Publication No, 2009-538215). The thread-fixing tool is configured to fix the suture thread by that the suture thread is inserted into the cylindrical member and the suture thread is sandwiched by an inner surface of the cylindrical member and an outer surface of the post-shaped member.

In the thread-fixing tool of the related art, in a process of fixing the suture thread, two members that sandwich the suture thread are slid with directional elements parallel to an insertion direction of the suture thread, and strong tension may be applied to the suture thread.

In addition, in the thread-fixing tool of the related art, since a force in a direction of moving the suture thread toward a biological tissue T is applied to the suture thread, the suture thread may move in a direction in which the suture thread hooked in the biological tissue T is loosened.

SUMMARY OF THE INVENTION

A first aspect of the present invention is a thread-fixing tool configured to fix a loop-shaped suture thread passing through a biological tissue. The thread-fixing tool including: a first member in which a lumen opened at an end surface so that the suture thread is inserted through the lumen, and a communication path having a first end opened at the end surface and a second end in communication with an intermediate portion of the lumen are formed; and a second member having a shaft portion inserted into the communication path of the first member, and a pressing portion which is formed at a distal portion of the shaft portion and which is capable of deforming outwardly in a radial direction of the shaft portion. The pressing portion is guided to the intermediate portion of the lumen through the communication path, and is deformed in a direction crossing an insertion direction of the suture thread to push the suture thread against an inner wall of the lumen.

According to a second aspect of the present invention, in the thread-fixing tool according to the first aspect of the present invention, the pressing portion may be deformed in a direction perpendicular to the insertion direction of the suture thread so as to fix the suture thread into the lumen when the second member is inserted into the communication path.

According to a third aspect of the present invention, in the thread-fixing tool according to the first aspect of the present invention, the pressing portion may include a protrusion having a restoring force that restores outwardly in the radial direction of the shaft portion, and the protrusion may be inserted into the lumen and the protrusion pushes the suture thread against the inner wall by a transformation of the protrusion from a state in which the protrusion is elastically deformed by a wall surface of the communication path and is inserted into the communication path to a state in which the protrusion is guided to the intermediate portion and is restored outwardly in the radial direction of the shaft portion.

According to a fourth aspect of the present invention, in the thread-fixing tool according to the first aspect of the present invention, the first member may include a guide wall surface forming a part of the communication path to guide the pressing portion to the intermediate portion, and configured to press the pressing portion in accordance with an insertion of the second member into the communication path, and the pressing portion may be inserted into the lumen and pushes the suture thread against the inner wall of the lumen, as the pressing portion is deformed outwardly in the radial direction of the shaft portion by being pressed from the guide wall surface.

According to a fifth aspect of the present invention, in the thread-fixing tool according to the first aspect of the present invention, the first member may have an outer circumferential surface formed along a longitudinal shaft of the lumen, the second member may have a connecting cover having an inner circumferential surface formed along the outer circumferential surface, and the connecting cover may be fitted onto the outer circumferential surface of the first member at a position at which the pressing portion is inserted into the lumen.

DETAILED DESCRIPTION OF THE INVENTION (First Embodiment)

A thread-fixing tool according to a first embodiment of the present invention will be described.

Figure 1:
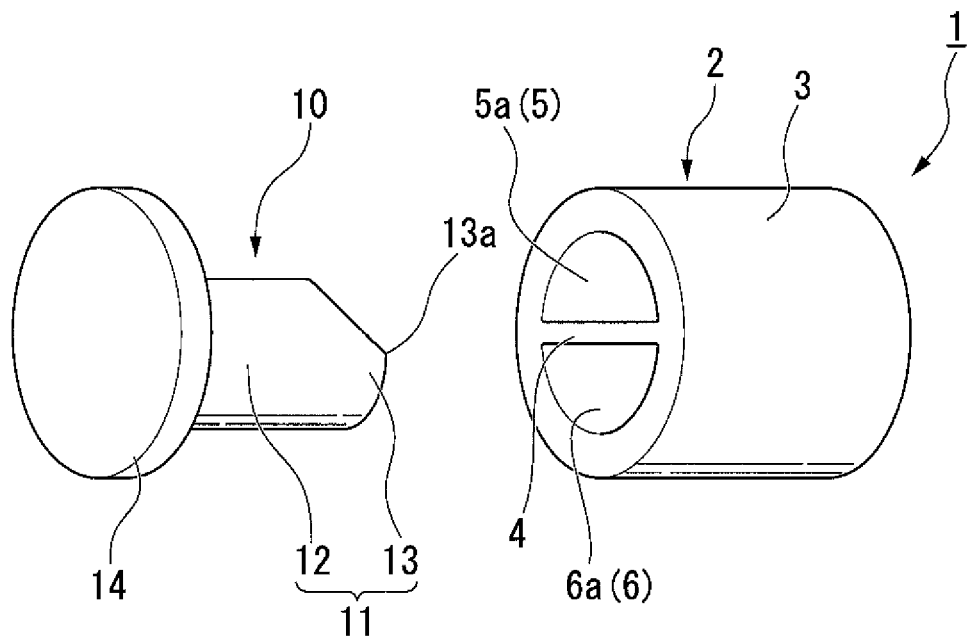
FIG. 1 is a perspective view showing a thread-fixing tool according to a first embodiment of the present invention.
Figure 2:
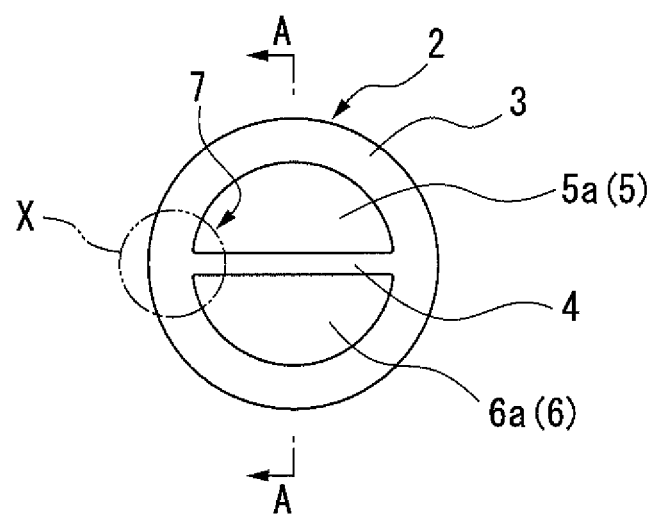
FIG. 2 is a front view of a first member of the thread-fixing tool according to the first embodiment of the present invention.
Figure 3:
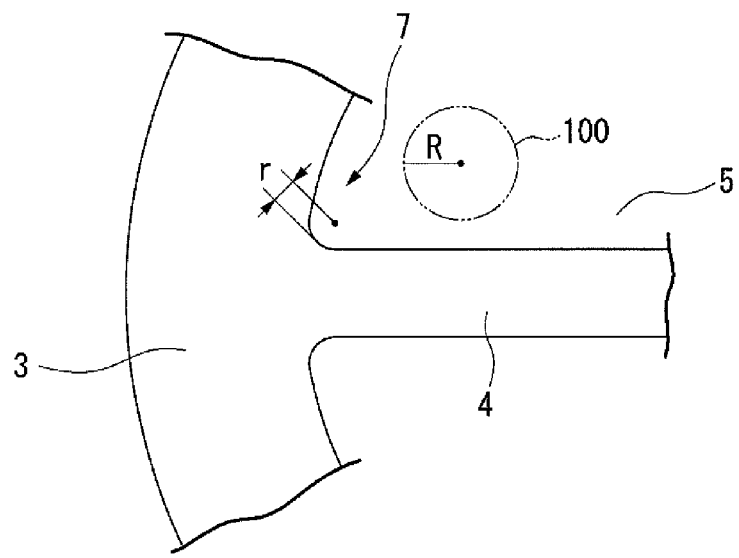
FIG. 3 is a partially enlarged view of FIG. 2.
Figure 4:
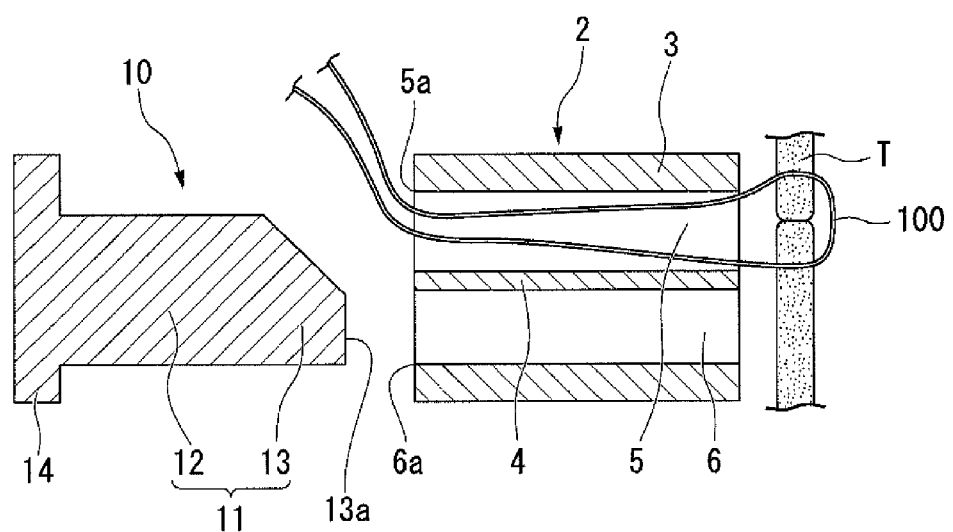
FIG. 4 is a cross-sectional view taken along line A-A of FIG. 2.

First, a constitution of the thread-fixing tool according to the embodiment will be described with reference to FIGS. 1 to 4. FIG. 1 is a perspective view showing the thread-fixing tool according to the embodiment. FIG. 2 is a front view of a first member of the thread-fixing tool according to the embodiment. FIG. 3 is a partially enlarged view of FIG. 2. FIG. 4 is a cross-sectional view taken along line A-A of FIG. 2.

The thread-fixing tool according to the embodiment is a medical instrument configured to fix a medical suture thread (hereinafter, simply referred to as a "suture thread") to the inside of the body.

As shown in FIG. 1, a thread-fixing tool 1 includes a first member 2 and a second member 10. The first member 2 has a first lumen 5 and a second lumen 6. The second member 10 has an insertion convex portion 11 and a flange portion 14.

The first member 2 has a tubular main body portion 3 and a pressing portion 4. The pressing portion 4 is disposed in the main body 3 to divide a cavity in the main body 3 into two portions, and the first lumen 5 and the second lumen 6 are formed in the main body 3 by the pressing portion 4. The first lumen 5 is opened at both end surfaces of the first member 2 in a central axial direction of the first member 2 (see FIG. 4). In addition, the second lumen 6 is opened at both end surfaces of the first member 2 in the central axial direction of the first member 2 (see FIG. 4). That is, in the embodiment, both of the first lumen 5 and the second lumen 6 are configured to form a through-hole extending parallel to a central axis of the first member 2.

In the embodiment, the first lumen 5 is a lumen having a first opening portion 5a through which a suture thread 100 (see FIG. 4) is inserted. The second lumen 6 is a lumen having a second opening portion 6a through which the insertion convex portion 11 is inserted. The first opening portion 5a and the second opening portion 6a are opened at different positions.

An exterior of the first member 2 is not particularly limited. Specifically, an exterior of the first member 2 may be formed in a columnar shape, a prismatic shape, a truncated conical shape, or the like. In addition, the exterior of the first member 2 preferably not has a protrusion or a sharp portion, which may harm the biological tissue T.

The main body 3 has stiffness such that a tubular shape is substantially maintained when the insertion convex portion 11 is inserted into the second lumen 6. The pressing portion 4 is preferably configured to be deformed by the insertion convex portion 11 when the insertion convex portion 11 is inserted into the second lumen 6. For example, the first member 2 has the main body 3, which is relatively thick, and the pressing portion 4, which is relatively thin. As a separate example, the first member 2 has the main body 3 formed of a hard material, and the pressing portion 4 formed of a material softer than the main body 3.

A metal, a resin, or the like, may be used as the material of the first member 2. Among these materials, a material having high biocompatibility is preferably used as the material of the first member 2. Specifically, stainless steel, titanium, polyether-ether-ketone, polylactic acid, or the like, may be used as the first member 2.

As shown in FIG. 3, when seen from the end surface side of the first member 2, the pressing portion 4 extends perpendicular to the main body 3 from an inner surface of the main body 3. In addition, a curved surface having a radius of curvature r smaller than a radius R of the suture thread 100 is formed at a connecting portion 7 between the main body 3 and the pressing portion 4. In addition, when the insertion convex portion 11 is inserted into the second lumen 6, the pressing portion 4 is deformed to approach the inner surface of the main body 3 in the first lumen 5 opposite to a side into which the insertion convex portion 11 is inserted (see FIG. 7). Accordingly, the connecting portion 7 between the main body 3 and the pressing portion 4 is deformed to have a clearance smaller than a diameter of the suture thread 100. In addition, a size of the clearance can be appropriately set by adjusting a size of the insertion convex portion 11.

The insertion convex portion 11 formed at the second member 10 is a member formed in order to deform the pressing portion 4 within the first member 2. The insertion convex portion 11 has stiffness greater than that of the pressing portion 4. In addition, the size of the insertion convex portion 11 is a size such that, when the insertion convex portion 11 is inserted into the second lumen 6, the pressing portion 4 is deformed toward the first lumen 5 so as to close the first lumen 5. Further, the size of the insertion convex portion 11 may be a size such that, when the insertion convex portion 11 is inserted into the second lumen 6, the pressing portion 4 is deformed toward the first lumen 5, and the first lumen 5 is closed by the pressing portion 4 to have a clearance slightly smaller than the diameter of the suture thread 100.

In the embodiment, the insertion convex portion 11 has a shaft portion 12 formed in a substantially columnar shape, and a tapered portion 13 formed opposite to a side at which the flange portion 14 is formed. Hereinafter, in the second member 10, the side at which the flange portion 14 is formed as a proximal end side in an insertion direction of the second member 10 and the side opposite to the side at which the flange portion 14 is formed as a distal side in the insertion direction of the second member 10 will be described.

The shaft portion 12 is configured to move the pressing portion 4 within the first member 2, and has a circular cross-sectional shape perpendicular to a central axis of the shaft portion 12. A diameter of the shaft portion 12 is configured to have a size such that the shaft portion 12 comes in contact with both of the main body 3 and the pressing portion 4 so as to deform the pressing portion 4 when the shaft portion 12 is inserted into the second lumen 6.

The tapered portion 13 is configured such that the exterior of the shaft portion 12 is gradually reduced toward the distal side in the insertion direction of the second member 10. A distal portion 13a of the tapered portion 13 is configured to have a size that can be inserted into the second lumen 6 without coming in contact with the inner surface of the second lumen 6 in a state in which the pressing portion 4 is not deformed. The distal portion 13a is configured to expand the second lumen 6 such that the shaft portion 12 can be inserted by the tapered portion 13.

The flange section 14 is a plate-shaped member having an area larger than an internal dimension of the second lumen 6. The flange portion 14 comes in contact with the first member 2 when the insertion convex portion 11 is completely inserted into the second lumen 6.

Figure 5:
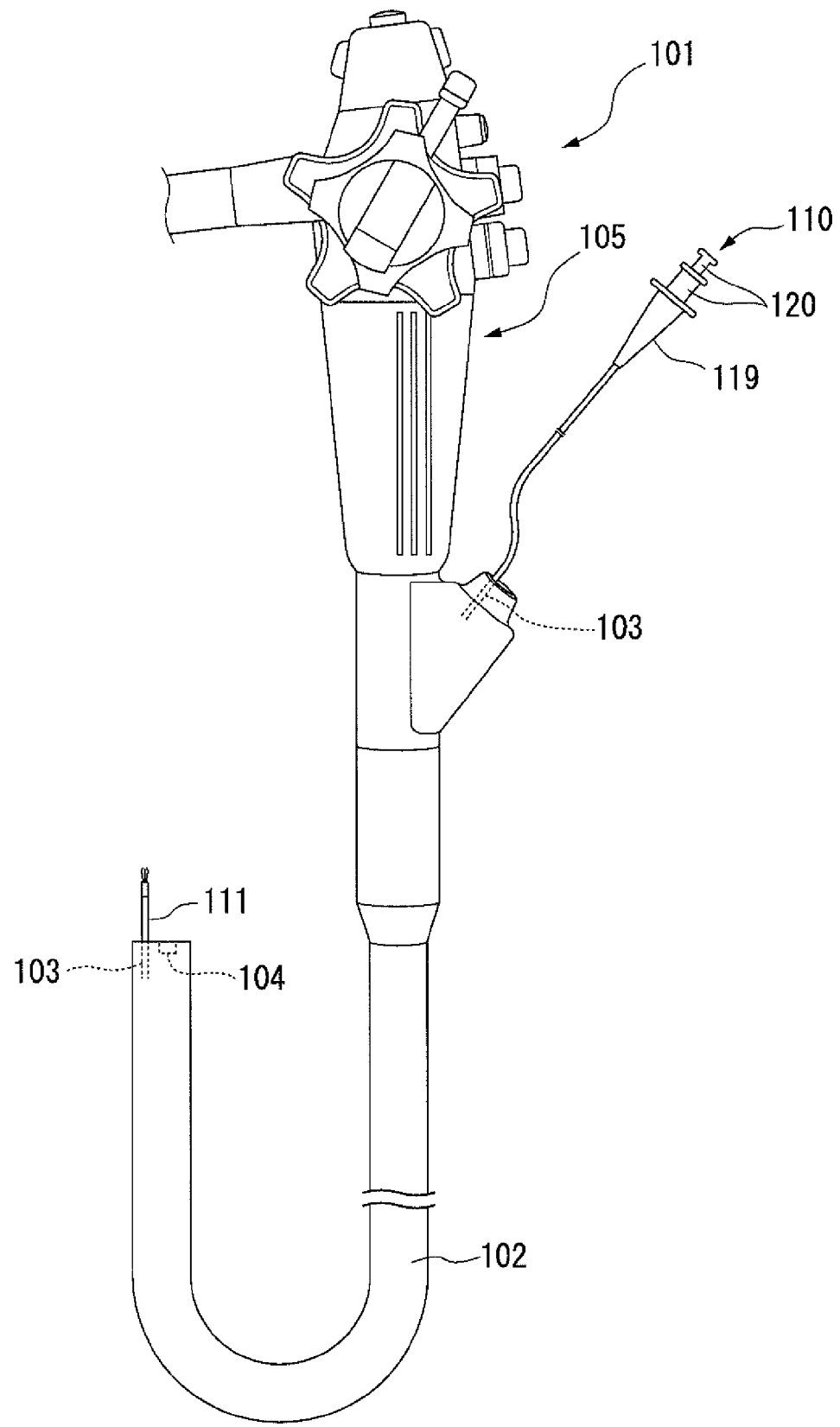
FIG. 5 is a view for describing a method of using the thread-fixing tool according to the first embodiment of the present invention.
Figure 6:
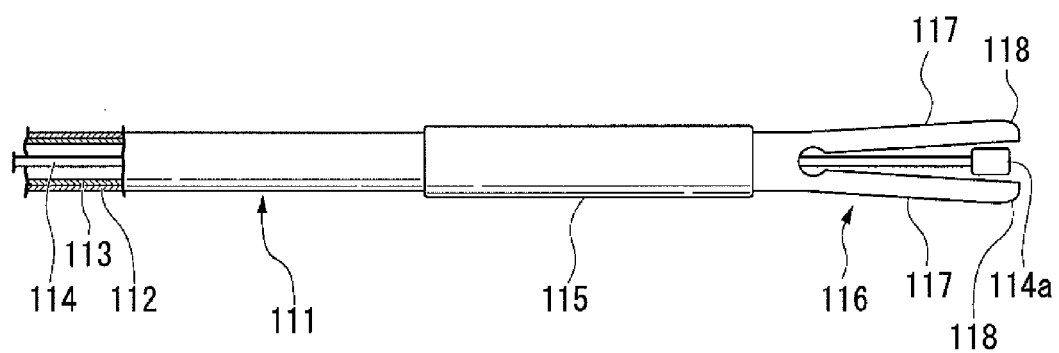
FIG. 6 is a schematic view showing a treatment tool for an endoscope used with the thread-fixing tool of the first embodiment according to the present invention.
Figure 7:
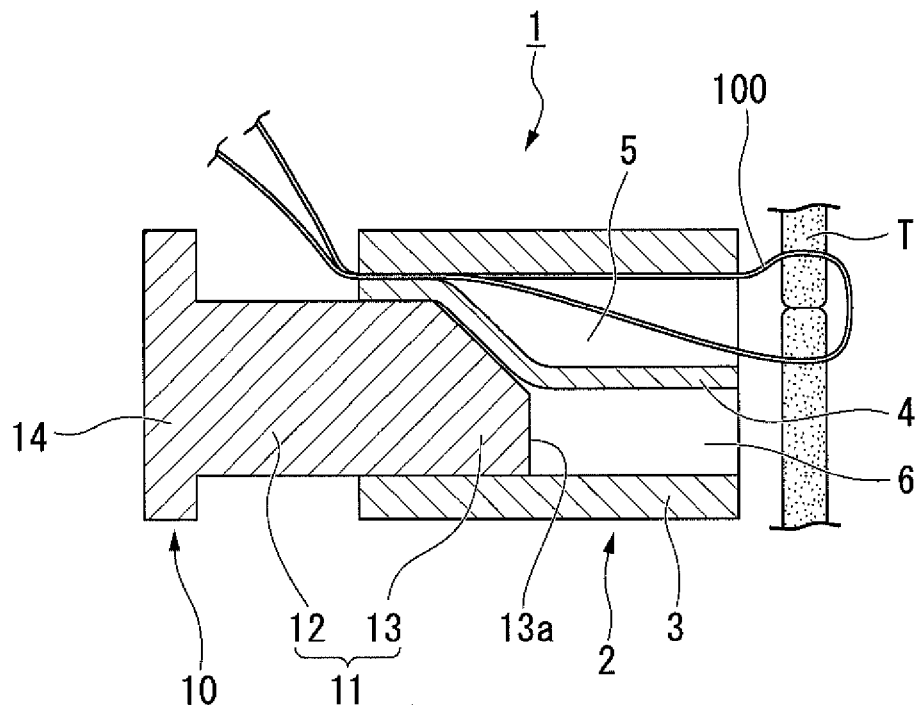
FIG. 7 is a cross-sectional view of the thread-fixing tool for describing the method of using the thread-fixing tool according to the first embodiment of the present invention.
Figure 8:
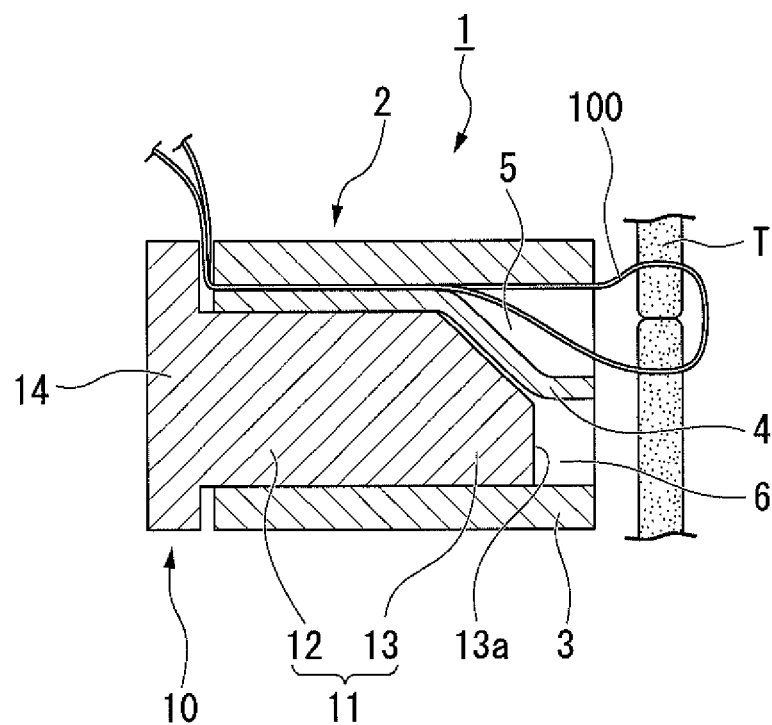
FIG. 8 is a cross-sectional view for describing an operation of the thread-fixing tool according to the first embodiment of the present invention.

Next, a method of using the thread-fixing tool according to the embodiment and an action of the thread-fixing tool will be described. FIG. 5 is a view for describing the method of using the thread-fixing tool. FIG. 6 is a schematic view showing a treatment tool for an endoscope used with the thread-fixing tool. FIG. 7 is a cross-sectional view of the thread-fixing tool for describing the method of using the thread-fixing tool. FIG. 8 is a cross-sectional view for describing the action of the thread-fixing tool.

The thread-fixing tool 1 according to the embodiment is used with, for example, an endoscope apparatus 101 inserted into the alimentary canal and a treatment tool 110 for an endoscope (see FIG. 5). In the embodiment, the action of the thread-fixing tool 1 will be described using an example in which the endoscope apparatus 101 is inserted into the stomach from the mouth, and the suture thread 100 that sutures the tissue of the stomach is fixed in the stomach.

First, the constitution of the endoscope apparatus 101 and the treatment tool 110 for the endoscope used in the embodiment will be simply described.

As shown in FIG. 5, the endoscope apparatus 101 exemplified in the embodiment includes an insertion portion 102 having flexibility, a treatment tool channel 103, an imaging unit 104, and a manipulation portion 105. The treatment tool channel 103 through which the treatment tool 110 for the endoscope is inserted is formed in the insertion portion 102. The imaging unit 104 is installed at a distal end of the insertion portion 102. The manipulation portion 105 is installed at a proximal end of the insertion portion 102.

In addition, the treatment tool 110 for the endoscope exemplified in the embodiment includes a flexible portion 111 inserted into the treatment tool channel 103, and a manipulation portion 119 installed at a proximal end of the flexible portion 111.

As shown in FIG. 6, the flexible portion 111 has an outer sheath 112, an inner sheath 113 inserted into the outer sheath 112, and a push rod 114 inserted into the inner sheath 113. A distal barrel 115 configured to open and close a grip portion 116 (to be described below) is installed at a distal end of the outer sheath 112. The grip portion 116 that can be opened and closed is installed at a distal end of the inner sheath 113. A distal end of the push rod 114 is formed in a plate shape having a surface perpendicular to a central axis of the push rod 114.

The grip portion 116 is fixed to the inner sheath 113 at a proximal end side thereof and has a plurality of grip pieces 117. The grip piece 117 extends so as to be gradually spaced apart from the central axis of the inner sheath 113 outwardly in a radial direction toward the distal end side. The distal end of the grip piece 117 has a claw 118 curved to extend toward the central axis of the inner sheath 113 and configured to hold the first member 2. The grip portion 116 is closed by drawing the plurality of grip pieces 117 into the distal barrel 115. In addition, the grip portion 116 is opened by pushing the plurality of grip pieces 117 from the distal barrel 115. The thread-fixing tool 1 according to the embodiment is disposed in a space surrounded by the plurality of grip pieces 117.

A distal end 114a of the push rod 114 can advance and retreat in a space surrounded by the plurality of grip pieces 117 in the central axial direction of the push rod 114 by a predetermined manipulation in the manipulation portion 119.

The manipulation portion 119 includes a sliding mechanism 120 configured to move the inner sheath 113 and the push rod 114 with respect to the outer sheath 112 and move the push rod 114 with respect to the inner sheath 113.

Next, a thread-fixing method using the endoscope apparatus 101, the treatment tool 110 for the endoscope and the thread-fixing tool 1 according to the embodiment will be described.

As shown in FIG. 7, for example, in the stomach, the suture thread 100 is reciprocated in a loop shape to pass through the stomach wall (the biological tissue T) by a known treatment using the endoscope or the suture needle. Next, a user grips the end portion of the suture thread 100 passing through the biological tissue T using a grip forceps or the like and extracts the end portion to the outside of the body via the treatment tool channel 103.

Next, the end portion of the suture thread 100 extracted to the outside of the body passes through the first lumen 5 formed in the first member 2. Further, after that, the thread-fixing tool 1 is attached to the treatment tool 110 for the endoscope.

The thread-fixing tool 1 is attached to the grip portion 116 of the treatment tool 110 for the endoscope. In this case, the first member 2 and the second member 10 are disposed in parallel in a space surrounded by the plurality of grip pieces 117 such that the second member 10 is disposed at the proximal end side of the first member 2. In a state in which the first member 2 and the second member 10 are disposed in parallel in the space surrounded by the plurality of grip pieces 117, when the grip portion 116 is inserted into the distal barrel 115, the first member 2 is held by the grip pieces 117 and the claw 118. Accordingly, the thread-fixing tool 1 is attached to the treatment tool 110 for the endoscope.

When the thread-fixing tool 1 is attached to the treatment tool 110 for the endoscope, the treatment tool 110 for the endoscope is inserted into the stomach through the treatment tool channel 103 of the endoscope apparatus 101. Accordingly, the thread-fixing tool 1 is introduced into the stomach.

After that, a distance between the first member 2 and the stomach wall, and tension of the suture thread 100 are appropriately adjusted. After that, the second member 10 is pushed into the second lumen 6 through the second opening portion 6a formed in the first member 2 by the distal end 114a of the push rod 114. Here, the insertion convex portion 11 formed at the second member 10 is inserted into the first member 2 from the second opening portion 6a formed in the first member 2. Further, an inner cavity of the second lumen 6 is forcedly extended by the tapered portion 13 formed at the insertion convex portion 11. Here, since the pressing portion 4 of the first member 2 is more flexible than the main body 3 of the first member 2, the pressing portion 4 is pressed by the insertion convex portion 11 to be deformed. That is, the pressing portion 4 is deformed such that a capacity of the first lumen 5 is reduced. In a process in which the insertion convex portion 11 is inserted into the first member 2, the pressing portion 4 is deformed to be curved in a direction perpendicular to the insertion direction of the suture thread 100 by the insertion convex portion 11. Then, the pressing portion 4 deformed to be curved in the insertion direction of the suture thread 100 presses the suture thread 100 against the inner wall of the first lumen 5. As a result, the suture thread 100 is fixed to the first member 2 by a frictional force between the inner wall of the first lumen 5 and the suture thread 100.

As shown in FIG. 8, in a state in which the insertion convex portion 11 is completely inserted into the second lumen 6, the insertion convex portion 11 is held so as to not fall out of the second lumen 6 by the frictional force between the shaft portion 12 of the insertion convex portion 11 and the inner surface of the second lumen 6. As the suture thread 100 is fixed by the thread-fixing tool 1, the biological tissue T is sutured.

The thread-fixing tool 1 according to the embodiment is deformed by bending the pressing portion 4 in a direction perpendicular to the insertion direction of the suture thread 100. For this reason, in a process in which the pressing portion 4 presses the suture thread 100, a force of moving the suture thread 100 in the insertion direction of the suture thread 100 is not applied to the suture thread 100. Accordingly, the suture thread 100 can be fixed with a sufficient fixing force, without applying a force in a direction in which the suture thread 100 is broken.

Further, since the suture thread 100 is pressed by the pressing portion 4 deformed to be bent in the direction perpendicular to the insertion direction of the suture thread 100, the suture thread 100 does not move in the insertion direction of the suture thread 100 and the suture thread 100 is prevented from loosening.

In addition, since the suture thread 100 can be fixed by simply inserting the insertion convex portion 11 of the second member 10 into the second lumen 6 of the first member 2, the suture thread 100 can be easily fixed.

MODIFIED EXAMPLE 1-1

Figure 9:
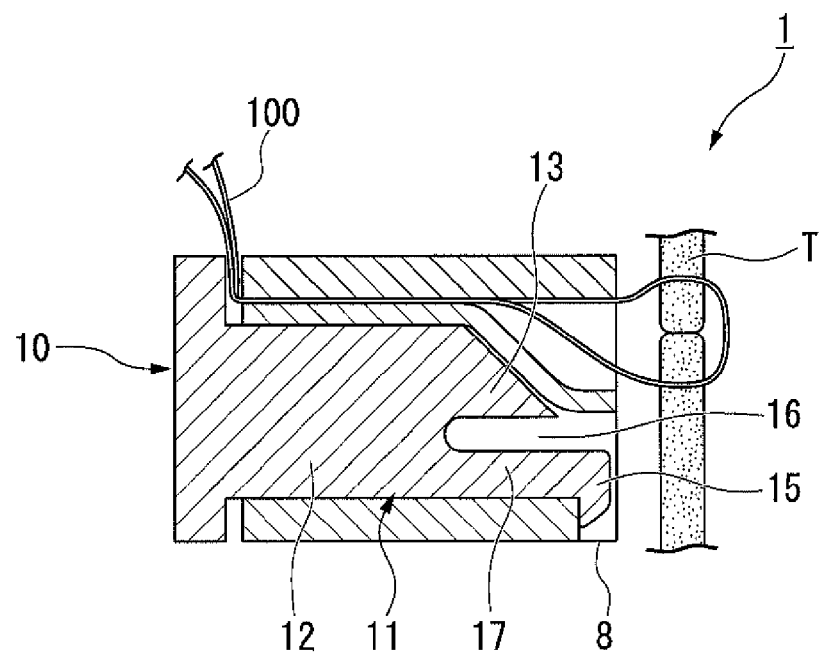
FIG. 9 is a cross-sectional view showing a constitution according to a modified example of the first embodiment of the present invention.
Figure 10:
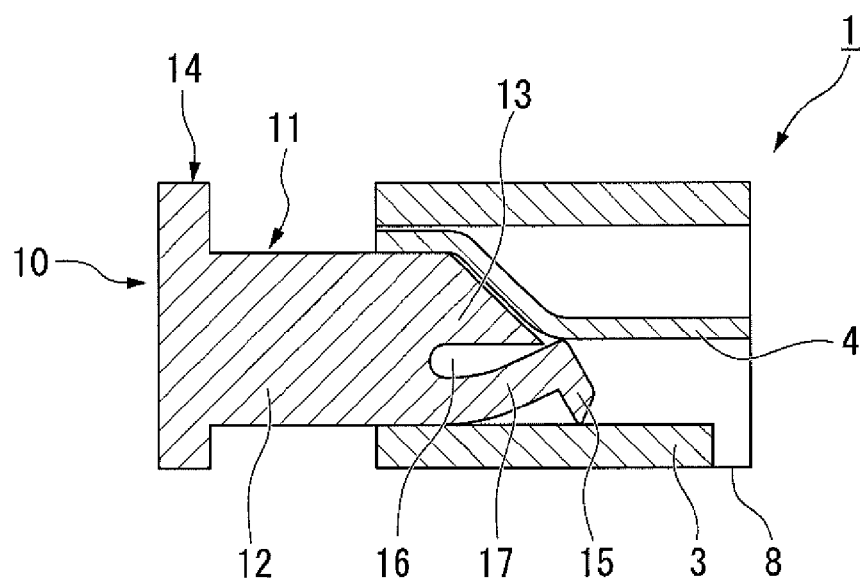
FIG. 10 is a cross-sectional view for describing the operation of the thread-fixing tool according to the modified example of the first embodiment of the present invention.

Next, a modified example of the first embodiment will be described. FIG. 9 is a cross-sectional view showing a constitution of the modified example. FIG. 10 is a cross-sectional view for describing an action of the thread-fixing tool according to the modified example.

As shown in FIG. 9, in the modified example, in the first member 2, a locking concave portion 8 for locking the insertion convex portion 11 is formed in one end portion in the central axial direction of the first member 2. In both ends in the central axial direction of the first member 2, an end portion of a side at which the locking concave portion 8 is formed is disposed toward the biological tissue T during use of the thread-fixing tool 1. The locking concave portion 8 is formed at the lumen (the second lumen 6 according to the modified example) side into which the insertion convex portion 11 is inserted.

In addition, in the shaft portion 12, a locking protrusion 15 inserted into the locking concave portion 8 and a slit 16 extending in parallel to the central axis of the shaft portion 12 are formed at the distal side in the insertion direction of the second member 10. In the modified example, the side at which the locking protrusion 15 is formed has elasticity at the distal side of the shaft portion 12 by the slit 16. Hereinafter, a portion of the distal side of the shaft portion 12 at which the locking protrusion 15 is formed is referred to as "a protrusion-forming region 17." The elasticity of the protrusion-forming region 17 differs according to a material of the shaft portion 12, a position of the slit 16, and a size of the slit 16. In the modified example, the proximal end of the slit 16 is disposed at the proximal end of the tapered portion 13 in the central axial direction of the shaft portion 12.

The locking protrusion 15 protrudes outwardly from the outer surface of the shaft portion 12 in the radial direction of the shaft portion 12. A protrusion length of the locking protrusion 15 is smaller than a thickness of the main body 3 of the first member 2. Accordingly, when the locking protrusion 15 is locked to the locking concave portion 8, the protruding end of the locking protrusion 15 is disposed inside the outer circumferential surface of the main body 3 of the first member 2.

In use of the thread-fixing tool 1 according to the modified example, the first member 2 is disposed such that the locking concave portion 8 formed in the first member 2 is faced to the stomach wall (the biological tissue T) side. Further, in a process in which the insertion convex portion 11 is inserted into the second lumen 6, the locking protrusion 15 comes in contact with the inner surface of the second lumen 6. When the insertion convex portion 11 is further inserted into the second lumen 6 from this state, as shown in FIG. 10, since the protrusion-forming region 17 is elastically deformed, the insertion convex portion 11 is inserted into the second lumen 6 while the locking protrusion 15 is in contact with the inner surface of the second lumen 6. When the locking protrusion 15 arrives at the locking concave portion 8, the locking protrusion 15 is inserted into the locking concave portion 8 by elasticity of the protrusion-forming region 17. Once the locking protrusion 15 is inserted into the locking concave portion 8, the locking protrusion 15 remains in the locking concave portion 8 unless an external force is applied to push the locking protrusion 15 into the second lumen 6. In this way, the locking protrusion 15 and the locking concave portion 8 function as a stopper configured to prevent the second member 10 from falling out of the second lumen 6 of the first member 2.

According to the constitution of the modified example, as the locking protrusion 15 moves into the locking concave portion 8, the suture thread 100 can be fixed with a sufficient fixing force while suppressing the probability of removing the second member 10 from the first member 2 to a low level.

In addition, in the thread-fixing tool 1 according to the modified example, the locking concave portions 8 may be formed at both of side of the first lumen 5 and side of the second lumen 6. In this case, any one of the first lumen 5 and the second lumen 6 may be arbitrarily selected to allow insertion of the suture thread 100, and the insertion convex portion may be inserted into the other lumen.

MODIFIED EXAMPLE 1-2

Figure 11:
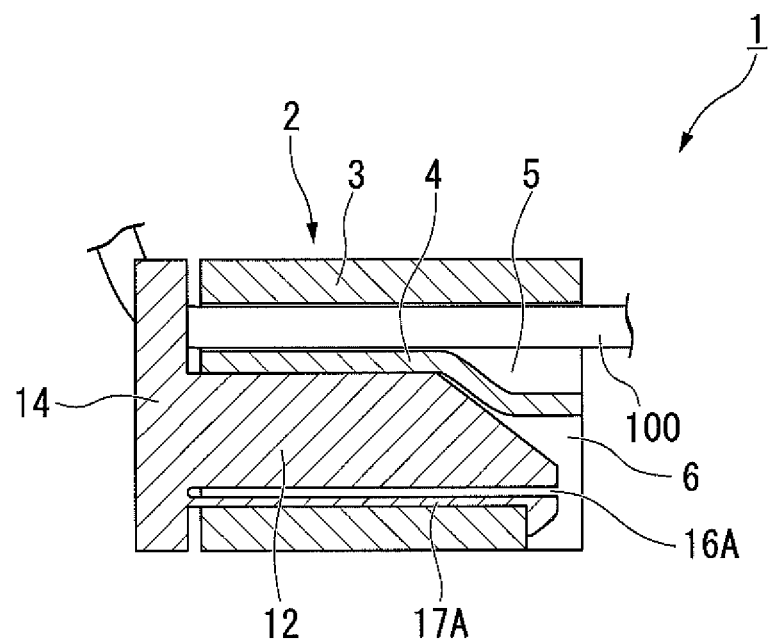
FIG. 11 is a cross-sectional view showing a constitution according to another modified example of the first embodiment of the present invention.
Figure 12:
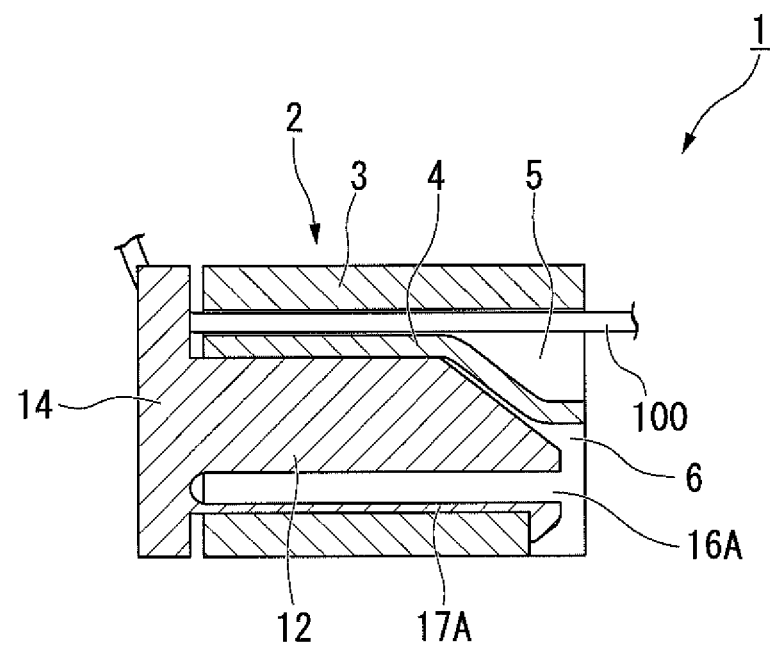
FIG. 12 is a cross-sectional view for describing the action of the thread-fixing tool according to the modified example of the first embodiment of the present invention.

Next, another modified example of the first embodiment will be described. FIG. 11 is a cross-sectional view showing a constitution of the modified example. FIG. 12 is a cross-sectional view for describing an action of the thread-fixing tool 1 according to the modified example.

In this modified example, instead of the slit 16, a slit 16A is formed in the shaft portion 12 at a different position.

The slit 16A extends to the proximal end of the shaft portion 12. That is, the protrusion-forming region 17A having elasticity is formed throughout the entire length in the central axial direction of the shaft portion 12. In the modified example, when the pressing portion 4 is pressed by the shaft portion 12, the protrusion-forming region 17A is elastically deformed to reduce a gap of the slit 16A. Here, the pressing force of the suture thread 100 by the pressing portion 4 becomes a predetermined pressing force as the protrusion-forming region 17A is elastically deformed. For example, with respect to the relatively thin suture thread 100 and the relatively thick suture thread 100, a substantially equal pressing force can be applied to the suture thread 100 from the pressing portion 4. In addition, with respect to the relatively hard suture thread 100 and the relatively soft suture thread 100, deformation of the suture thread 100 is compensated by elastic deformation of the protrusion-forming region 17A so that substantially the same pressing force can be applied to the suture thread 100 from the pressing portion 4.

In the modified example, a range of a thickness and hardness of the suture thread 100 that can be used by one kind of thread-fixing tool 1 is wide, and use convenience is improved.

(Second Embodiment)

A thread-fixing tool according to a second embodiment of the present invention will be described. In addition, in the embodiments to be described below and modified examples thereof, the same components as those described in the above-mentioned embodiment and the modified example thereof are designated by the same reference numerals, and description thereof will not be repeated.

Figure 13:
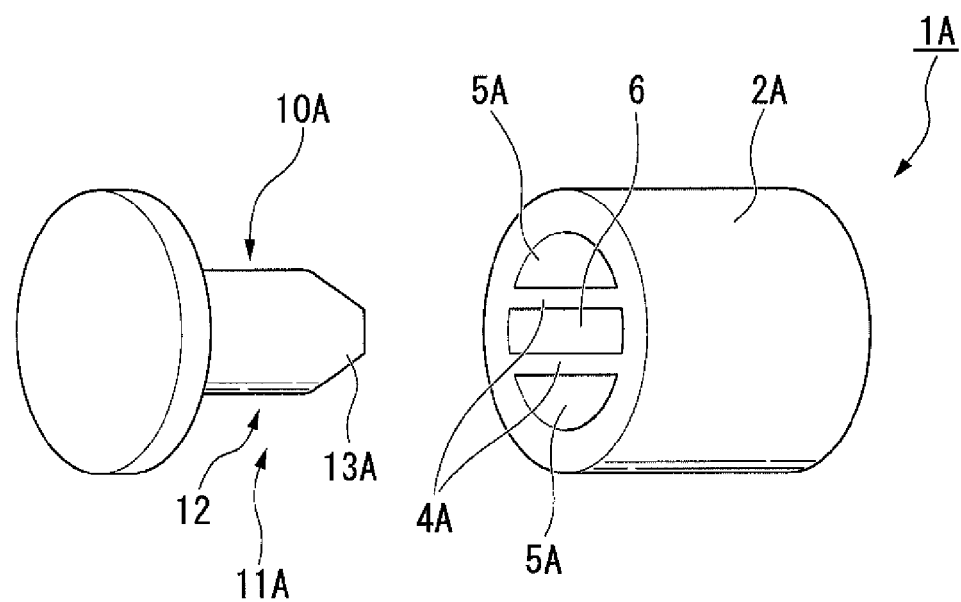
FIG. 13 is a perspective view showing a thread-fixing tool according to a second embodiment of the present invention.
Figure 14:
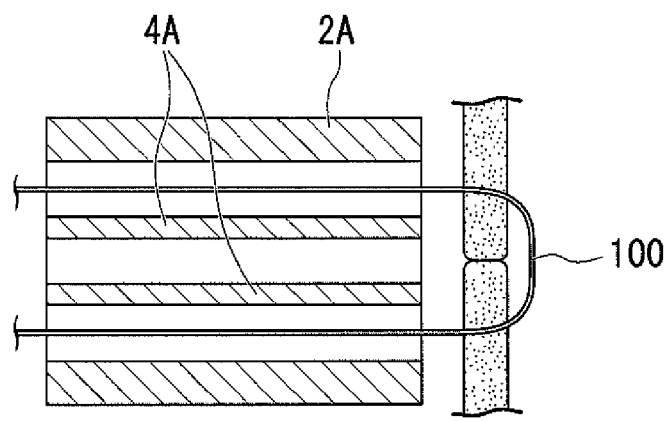
FIG. 14 is a cross-sectional view showing a first member of the thread-fixing tool according to the second embodiment of the present invention.

First, a constitution of a thread-fixing tool 1A according to the embodiment will be described with reference to FIGS. 13 and 14. FIG. 13 is a perspective view showing the thread-fixing tool 1A according to the embodiment. FIG. 14 is a cross-sectional view showing a first member in the thread-fixing tool 1A.

The thread-fixing tool 1A according to the embodiment includes a first member 2A having two first lumens 5A having the same shape as the first lumen 5 described in the first embodiment, and a second member 10A having a different shape from the second member 10 described in the first embodiment.

The two first lumens 5A formed in the first member 2A are disposed at both sides to sandwich the second lumen 6 therebetween. Pressing portions 4A that can be deformed in the same manner as in the pressing portion 4 described in the first embodiment are disposed between the first lumens 5A and the second lumen 6. In the embodiment, the pressing portions 4A are formed at two places in the main body 3.

The second member 10A includes an insertion convex portion 11A. A tapered portion 13A having a different shape from the tapered portion 13 described in the first embodiment is formed at the insertion convex portion 11A. The tapered portion 13A according to the embodiment has a set of inclined surfaces inclined in directions symmetrical with respect to a central axis of the shaft portion 12. When the tapered portion 13A is inserted into the second lumen 6 by the set of inclined surfaces formed at the tapered portion 13A, the inner cavity of the second lumen 6 can be expanded by simultaneously deforming the two pressing portions 4A.

Figure 15:
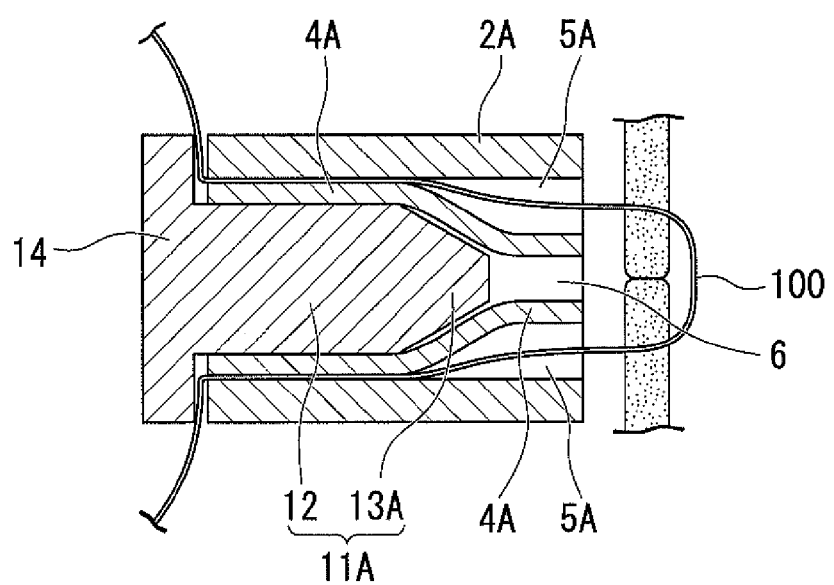
FIG. 15 is a cross-sectional view for describing an action of the thread-fixing tool according to the second embodiment.

Next, a method of using the thread-fixing tool 1A and an action of the thread-fixing tool 1A will be described. FIG. 15 is a cross-sectional view for describing the action of the thread-fixing tool 1A.

In use of the thread-fixing tool 1A according to the embodiment, unlike the first embodiment, one end side and the other end side of the suture thread 100 are inserted into the two first lumens 5A one by one. After that, the insertion convex portion 11A is inserted into the second lumen 6, the pressing portion 4A is deformed by the tapered portion 13A formed at the insertion convex portion 11A, and the inner cavity of the first lumens 5A is closed. Here, one of the two pressing portions 4A presses one of the two suture threads 100, and the other of the two pressing portions 4A presses the other of the two suture threads 100. Accordingly, both of the two suture threads 100 are pressed against and fixed to the inner surface of the first lumen 5A by the pressing portions 4A.

For example, in use of the thread-fixing tool 1, the suture thread 100 is entangled in the first lumen 5. When the suture thread 100 in an entangled state is fastened, a pressing force is locally applied to the suture thread 100 so that the suture thread 100 may be cut. However, in the first embodiment, the entangling of the suture thread 100 can be solved in a step of adjusting tension of the suture thread 100 during use of the thread-fixing tool 1.

According to the thread-fixing tool 1A according to the embodiment, when the first lumens 5A are closed, since the first lumens 5A sandwich the one suture thread 100, the two suture threads 100 are not entangled in comparison with the case in which the two suture threads 100 are inserted into the same first lumen 5. Then, in the embodiment, when the first lumens 5A are closed, since the first lumens 5A sandwich the one suture thread 100, the suture thread 100 can be stably fixed.

MODIFIED EXAMPLE 2-1

Figure 16:
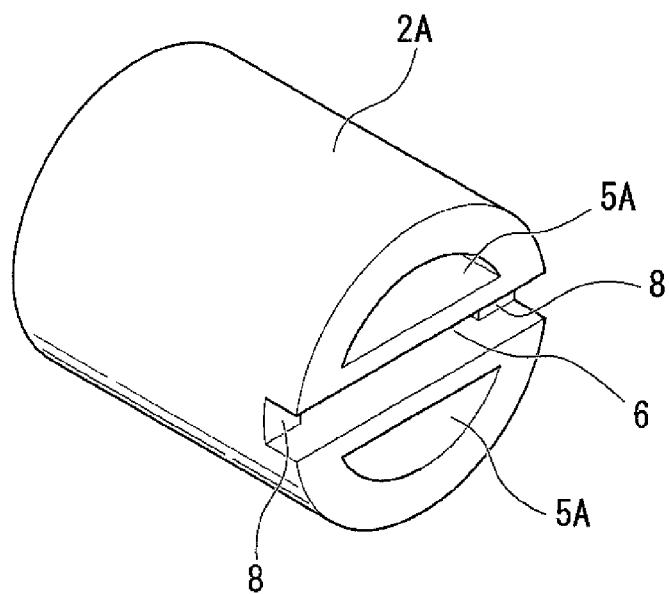
FIG. 16 is a perspective view of a first member, showing a constitution according to a modified example of the second embodiment of the present invention.
Figure 17:
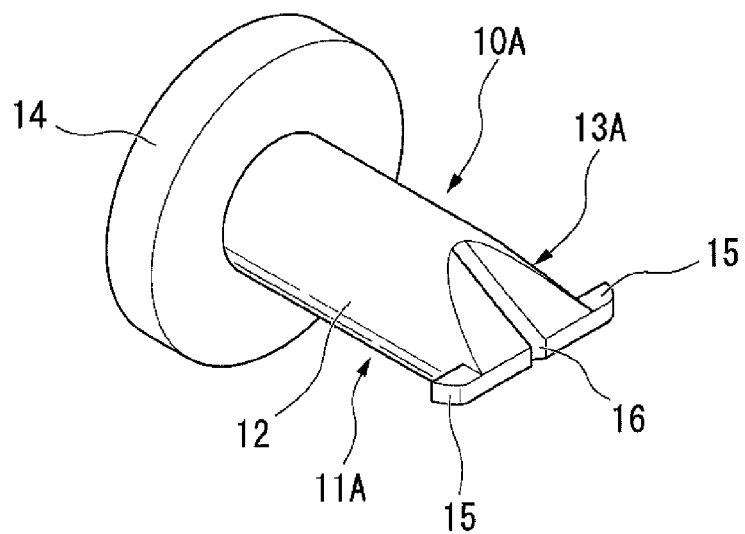
FIG. 17 is a perspective view of a second member, showing a constitution according to the modified example of the second embodiment of the present invention.

Next, a modified example of the second embodiment will be described. FIG. 16 is a perspective view of a constitution of the modified example, showing the first member 2A. FIG. 17 is a perspective view of a constitution of the modified example, showing the second member 10A.

As shown in FIGS. 16 and 17, in the modified example, the locking protrusion 15 described in the modified example 1-1 of the above-mentioned first embodiment is formed in the vicinity of the tapered portion 13A, and the slit 16 is formed at the tapered portion 13A. In addition, the locking concave portion 8 described in the modified example 1-1 of the above-mentioned first embodiment is formed at the first member 2A.

Even in the constitution shown in the modified example, like the modified example 1-1, the second member 10A cannot be easily removed from the second lumen 6.

(Third Embodiment)

A thread-fixing tool according to a third embodiment of the present invention will be described.

Figure 18:
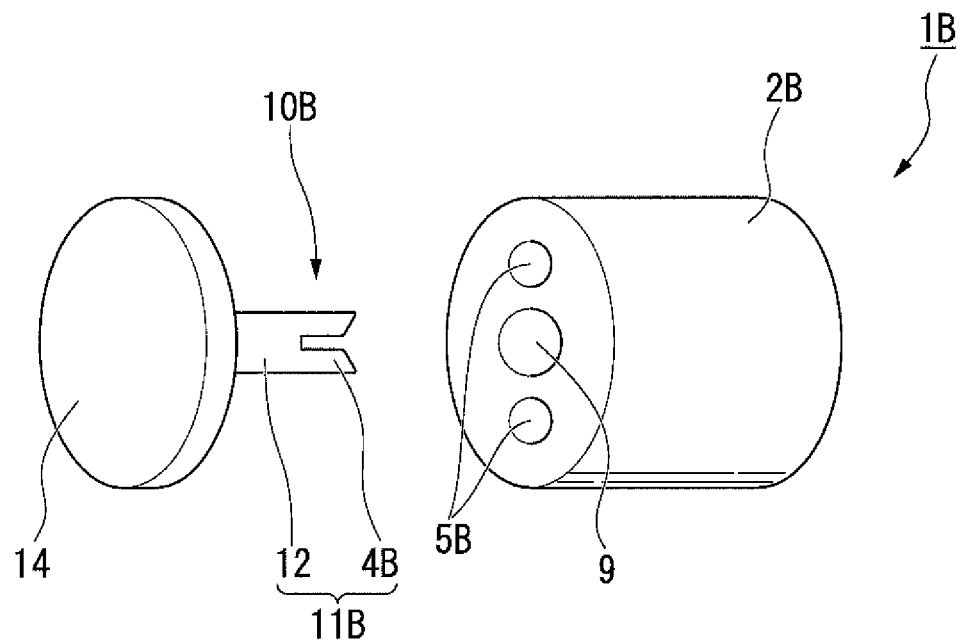
FIG. 18 is a perspective view showing a thread-fixing tool according to a third embodiment of the present invention.
Figure 19:
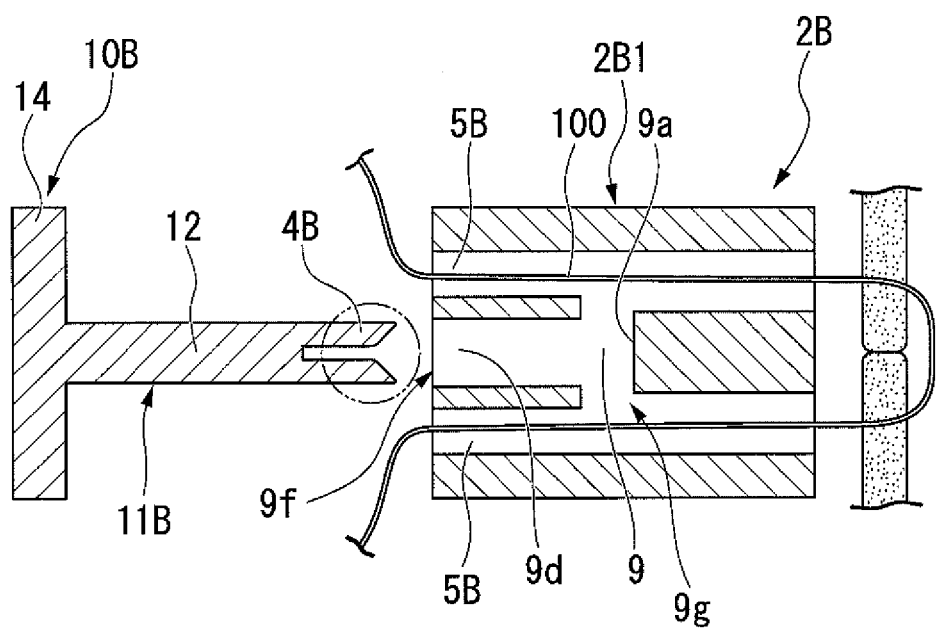
FIG. 19 is a cross-sectional view of the thread-fixing tool according to the third embodiment of the present invention.
Figure 20:
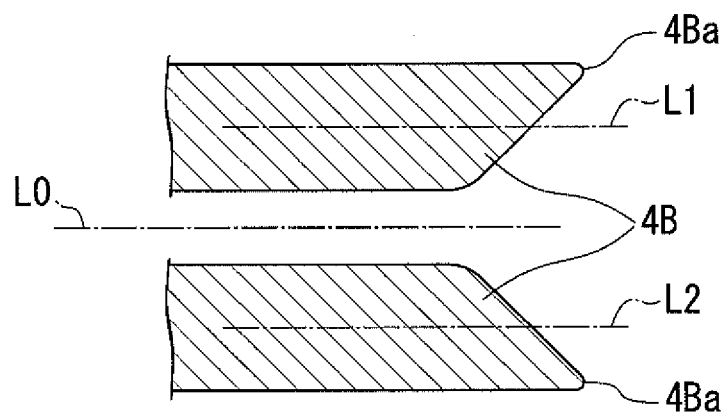
FIG. 20 is a partially enlarged view of a pressing section of FIG. 19.

First, a constitution of a thread-fixing tool 1B according to the embodiment will be described with reference to FIGS. 18 to 20. FIG. 18 is a perspective view showing the thread-fixing tool according to the embodiment. FIG. 19 is a cross-sectional view of the thread-fixing tool. FIG. 20 is a partially enlarged view of a pressing portion 4B of FIG. 19.

As shown in FIGS. 18 and 19, the thread-fixing tool 1B includes a first member 2B having through-holes (first lumens 5B) extending in the central axial direction and a communication path 9 in communication with the through-holes, and a second member 10B having an insertion convex portion 11B and a flange portion 14.

The two through-holes formed in the first member 2B are configured to sandwich the communication path 9 therebetween, and constitute the first lumens 5B through which the suture threads 100 are inserted one by one, like the first lumens 5A described in the second embodiment.

The communication path 9 has an opening portion 9d (a second opening portion) insertable into the insertion convex portion 11B of the second member 10B and a guide wall portion 9a having a surface perpendicular to the central axis of the first member 2B. The opening portion 9d is formed at one end side (a first end 90 in the central axial direction of the first member 2B. The guide wall portion 9a is formed at an intermediate portion 2B1 in the central axial direction of the first member 2B. The communication path 9 comes in communication with the first lumen 5B at a portion (a second end 9g) at the intermediate portion 2B1 in the central axial direction of the first member 2B and at which the guide wall portion 9a is formed. In the embodiment, the central axis of the communication path 9 is parallel to the central axis of the first member 2B.

The insertion convex portion 11B formed at the second member 10B has a shaft portion 12 having one end fixed to the flange portion 14, and a pressing portion 4B formed at the other end side of the shaft portion 12. The shaft portion 12 is a rod-shaped member inserted into the communication path 9 from the opening portion 9d. The pressing portion 4B is formed of a plastically deformable material, comes in contact with the guide wall portion 9a of the communication path 9, and is inserted into the first lumen 5B from the communication path 9 by being bent along the guide wall portion 9a. The same number of pressing portions 4B as that of the first lumens 5B are formed at the shaft portion 12. The pressing portions 4B are configured to be inserted into the first lumens 5B one by one. Each of the pressing portions 4B protrudes from the other end of the shaft portion 12 in the central axial direction of the shaft portion 12 in a state before being inserted into the communication path 9.

As shown in FIG. 20, a protruding end 4Ba side of each of the pressing portions 4B has an inclined surface rounded toward a central axis side L0 of the communication path 9. In addition, in the pressing portions 4B, the protruding ends 4Ba of the pressing portions 4B are offset to the side spaced apart from the central axis L0 of the communication path 9 with respect to the central axes L1 and L2 of the pressing portions 4B. Further, the protruding end 4Ba of each of the pressing portions 4B has a curved shape curved along a shape of the inner wall of the first lumen 5B. Accordingly, the protruding end 4Ba of the pressing portion 4 is adhered to the inner wall of the first lumen 5B when inserted into the first lumen 5B. Otherwise, the protruding end 4Ba of the pressing portion 4B is disposed to have a substantially constant clearance with respect to the inner wall of the first lumen 5B when inserted into the first lumen 5B. The clearance is smaller than the diameter of the suture thread 100 fixed by the thread-fixing tool 1B according to the embodiment.

Figure 21:
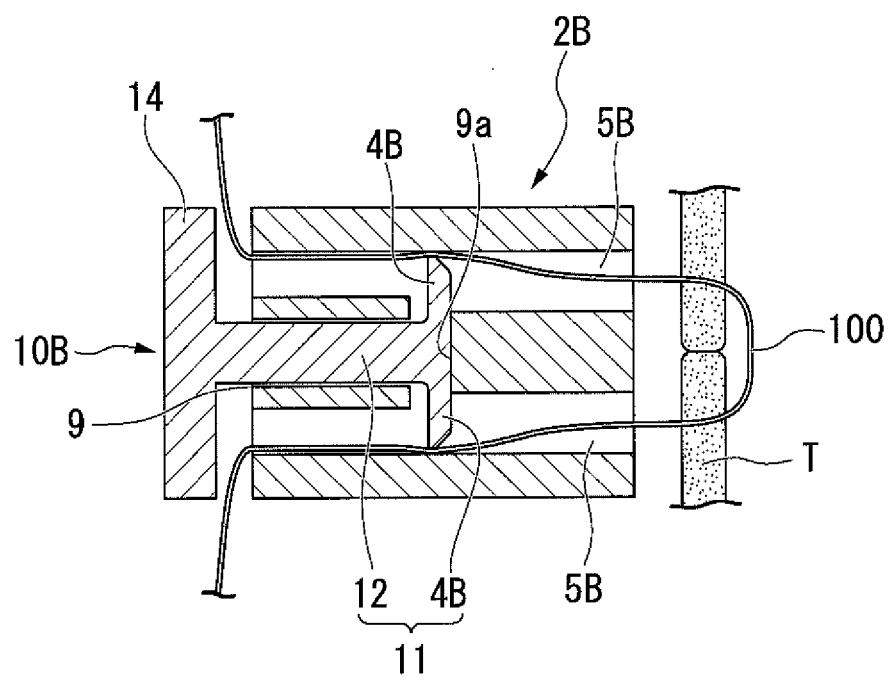
FIG. 21 is a cross-sectional view for describing an action of the thread-fixing tool according to the third embodiment of the present invention.

FIG. 21 is a cross-sectional view for describing an action of the thread-fixing tool.

As shown in FIG. 21, in a state in which the insertion convex portion 11B is completely inserted into the communication path 9, the pressing portion 4B comes in contact with the guide wall portion 9a and is curved toward the first lumen 5B. Then, the protruding end 4Ba of the pressing portion 4B is guided into the first lumen 5B and comes in contact with the inner wall of the first lumen 5B. In addition, in a state in which the insertion convex portion 11B is completely inserted into the communication path 9, the protruding end 4Ba of the pressing portion 4B has a clearance smaller than the diameter of the suture thread 100 with respect to the inner wall of the first lumen 5B, and is disposed in the first lumen 5B. Accordingly, when the suture thread 100 is disposed in the first lumen 5B, the suture thread 100 is pushed to the inner wall of the first lumen 5B by the protruding end 4Ba of the pressing portion 4B. As a result, the suture thread 100 is fixed by the thread-fixing tool 1B.

In addition, since the pressing portion 4B is disposed in the communication path 9 and the first lumen 5B in a state in which the pressing portion 4B is bent through plastic deformation, the second member 10B is not removed from the first member 2B because the pressing portion 4B is caught by the inner wall of the communication path 9.

Even in the embodiment, the pressing portion 4B presses the suture thread 100 in a direction perpendicular to the insertion direction of the suture thread 100. Accordingly, the suture thread 100 can be fixed with a sufficient fixing force without applying a force in a direction in which the suture thread 100 is broken.

MODIFIED EXAMPLE 3-1

Figure 22:
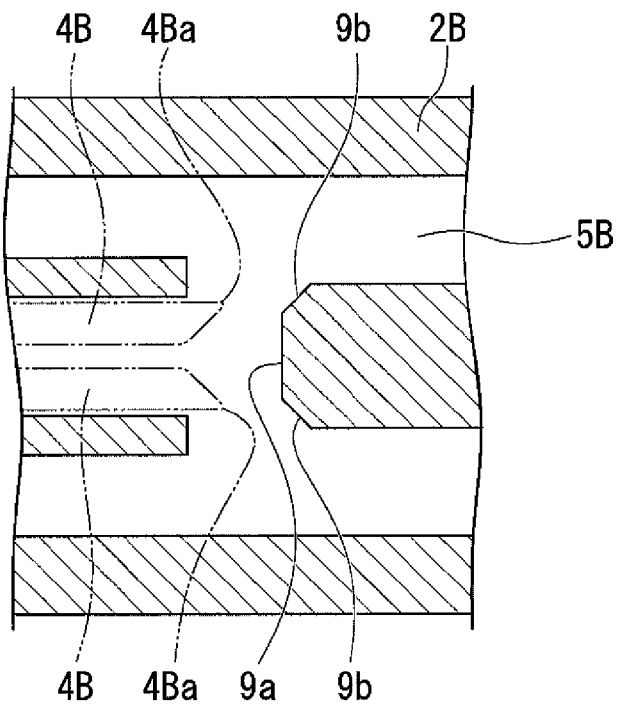
FIG. 22 is a partial cross-sectional view of a first member, showing a constitution according to a modified example of the third embodiment of the present invention.

Next, a modified example of the third embodiment will be described. FIG. 22 is a partial cross-sectional view of the first member 2B, showing a constitution of the modified example.

Figure 23:
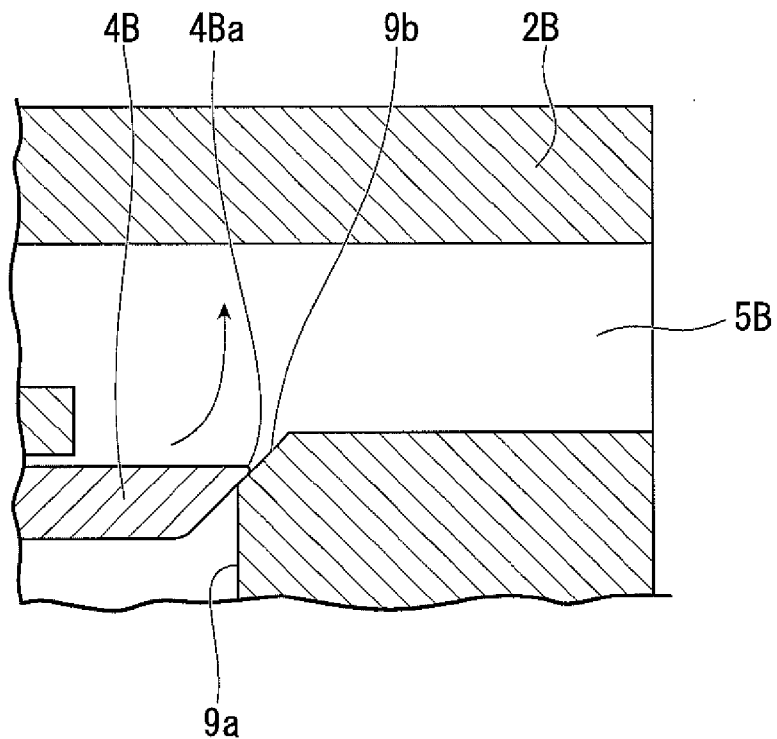
FIG. 23 is a partial cross-sectional view for describing an action of the first member according to the modified example of the third embodiment of the present invention.

FIG. 23 is a partial cross-sectional view for describing an action of the first member 2B according to the modified example.

As shown in FIGS. 22 and 23, in the modified example, a shape of the guide wall portion 9a is different from that of the above-mentioned third embodiment.

The guide wall portion 9a is chamfered at a connecting portion to the first lumen 5B. A vicinity of the protruding end 4Ba of the pressing portion 4B is configured to come in contact with a chamfered portion 9b of the guide wall portion 9a. Accordingly, the protruding end 4Ba of the pressing portion 4B is easily guided into the first lumen 5B.

MODIFIED EXAMPLE 3-2

Figure 24:
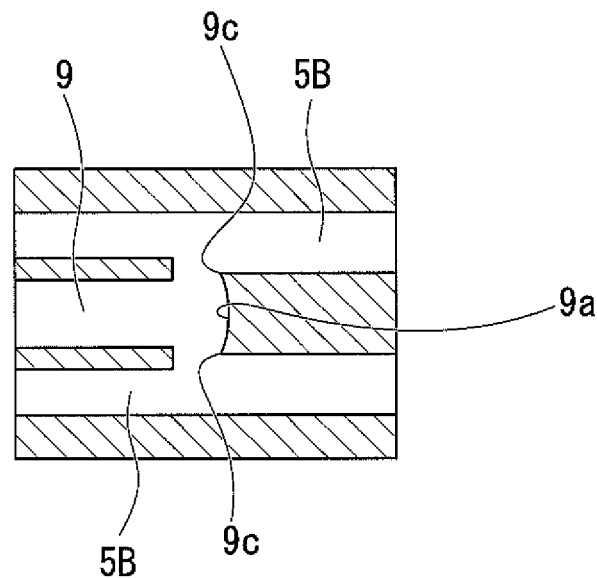
FIG. 24 is a cross-sectional view of a first member, showing a constitution according to another modified example of the third embodiment of the present invention.
Figure 25:
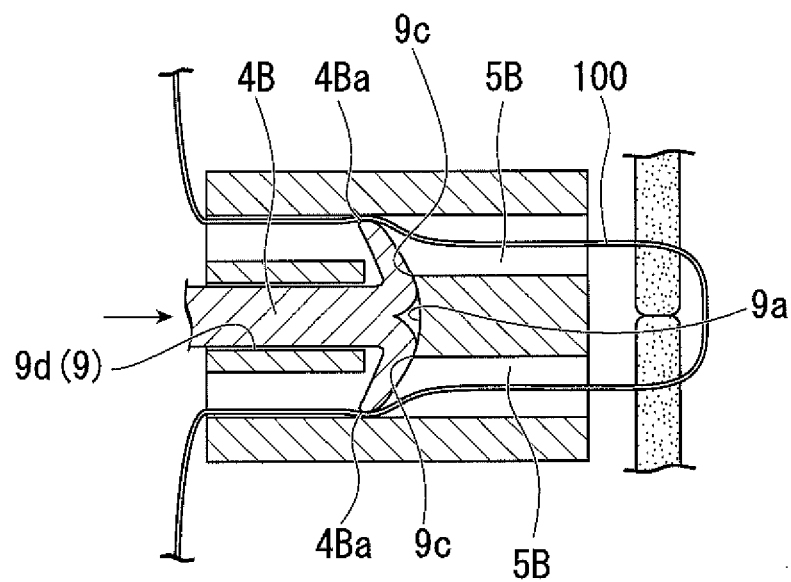
FIG. 25 is a cross-sectional view for describing an action of the first member according to the modified example of the third embodiment of the present invention.

Next, another modified example of the third embodiment will be described. FIG. 24 is a cross-sectional view of a first member, showing a constitution of the modified example. FIG. 25 is a cross-sectional view for describing an action of the first member according to the modified example.

As shown in FIG. 24, in the modified example, a shape of the guide wall portion 9a is different from that of the above-mentioned third embodiment.

In the connecting portion to the first lumen 5B, the guide wall portion 9a has an inclined surface 9c approaching the opening portion 9d as it goes outwardly in the radial direction of the communication path 9. The inclined surface 9c of the modified example guides the pressing portion 4B such that the protruding end 4Ba of the pressing portion 4B advances toward the opening portion 9d in the first lumen 5B. As shown in FIG. 25, each of the pressing portions 4B is bent in substantially a U shape by the inclined surface 9c.

In the modified example, after the protruding end 4Ba of the pressing portion 4B is guided into the first lumen 5B, the protruding end 4Ba of the pressing portion 4B presses the suture thread 100 in a direction crossing the insertion direction of the suture thread 100.

In the constitution of the modified example, in a state in which the suture thread 100 is pressed by the pressing portion 4B, when the suture thread 100 is moved in a direction in which the sutured state by the suture thread 100 is loosened, a pulling force is applied such that the pressing portion 4B penetrates the inner wall of the first lumen 5B. Here, since the pressing force with respect to the suture thread 100 is increased, the sutured state cannot be easily loosened. In addition, in a state in which the pressing force with respect to the suture thread 100 is increased in this way, the pressing portion 4B presses the suture thread 100 in a direction substantially perpendicular to the insertion direction of the suture thread 100. For this reason, the suture thread 100 cannot be easily cut even in a state in which the pressing force is increased.

(Fourth Embodiment)

A thread-fixing tool according to a fourth embodiment of the present invention will be described.

Figure 26:
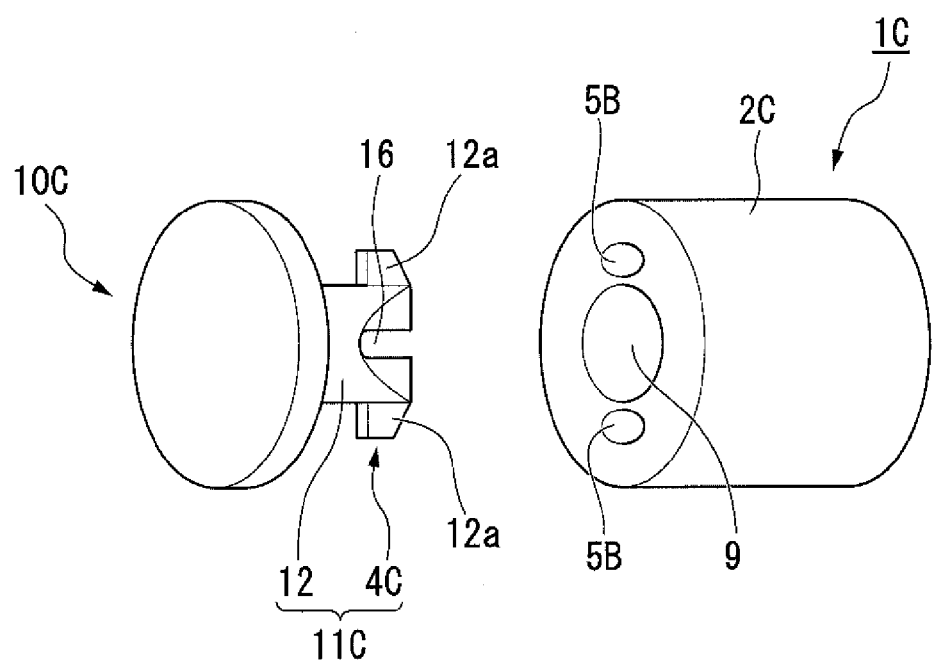
FIG. 26 is a perspective view showing a thread-fixing tool according to a fourth embodiment of the present invention.
Figure 27:
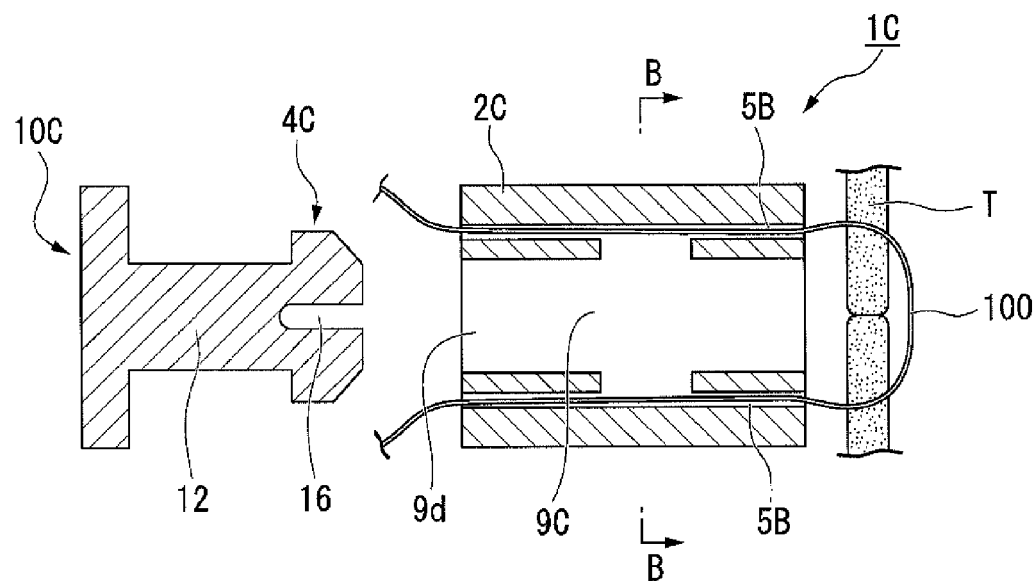
FIG. 27 is a cross-sectional view of the thread-fixing tool according to the fourth embodiment of the present invention.
Figure 28:
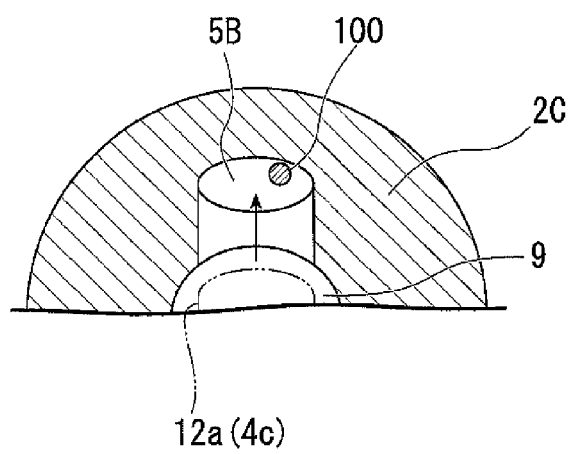
FIG. 28 is a partial cross-sectional view taken along line B-B of FIG. 27.

First, a constitution of a thread-fixing tool 1C according to the embodiment will be described with reference to FIGS. 26 to 28. FIG. 26 is a perspective view showing the thread-fixing tool 1C according to the embodiment. FIG. 27 is a cross-sectional view of the thread-fixing tool 1C. FIG. 28 is a partial cross-sectional view taken along line B-B of FIG. 27.

As shown in FIGS. 26 and 27, the thread-fixing tool 1C includes a first member 2C and a second member 10C. The first member 2C is different from the first member 2B described in the third embodiment. The second member 10C is partially different from the second member 10B described in the third embodiment.

As shown in FIG. 27, the first member 2C has a different shape from the first member 2B described in the third embodiment in that the guide wall portion 9a is not provided. In the embodiment, as shown in FIG. 26, a communication path 9C formed in the first member 2C is formed in a shape in which through-holes opened at both end surfaces in the central axial direction of the first member 2 are disposed between the first lumens 5B.

The second member 10C includes an elastically deformable pressing portion 4C instead of the elastically deformable pressing portion 4B described in the third embodiment. The pressing portion 4C is formed at a distal end of the shaft portion 12, and includes a protrusion 12a and a slit 16. The protrusion 12a is formed to protrude outwardly in the radial direction of the shaft portion 12 more than the outer surface of the shaft portion 12. The slit 16 is formed to extend in the central axial direction of the shaft portion 12.

The protrusion 12a is configured to be inserted into the first lumen 5B from the communication path 9 in a state in which the first member 2C is attached to the second member 10C. For example, like the third embodiment, the protrusion 12a comes in contact with the inner wall of the first lumen 5B. Alternatively, the protrusion 12a has a clearance equal to or smaller than the diameter of the suture thread 100 with respect to the inner wall of the first lumen 5B and disposed in the first lumen 5B.

In addition, as shown in FIG. 28, the protruding end of the protrusion 12a has a surface curved along a shape of the inner wall of the first lumen 5B. The protruding end of the protrusion 12a comes in line contact with the outer surface of the suture thread 100.

Figure 29:
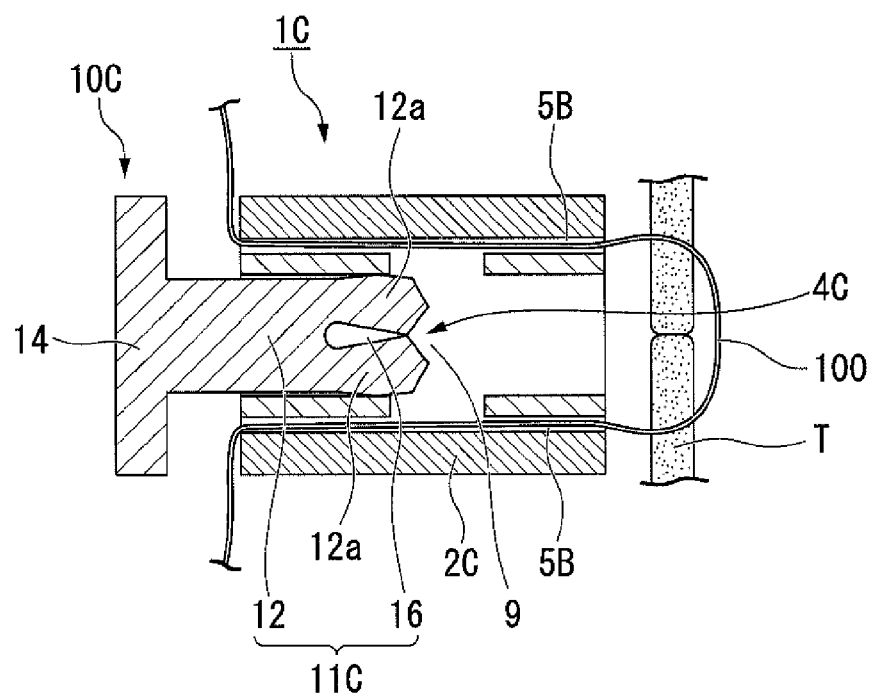
FIG. 29 is a cross-sectional view for describing an action of the thread-fixing tool according to the fourth embodiment of the present invention.
Figure 30:
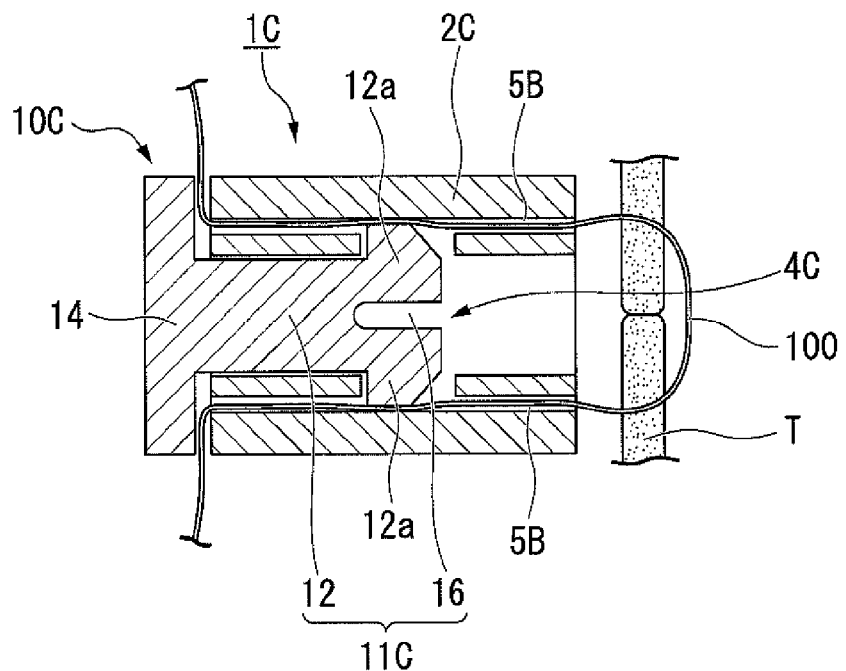
FIG. 30 is a cross-sectional view for describing an action of the thread-fixing tool according to the fourth embodiment of the present invention.

Next, an action of the thread-fixing tool according to the embodiment will be described. FIGS. 29 and 30 are cross-sectional views for describing the action of the thread-fixing tool 1C.

As shown in FIGS. 29 and 30, during use of the thread-fixing tool 1C according to the embodiment, in the second member 10C, when the insertion convex portion 11C is inserted into the opening portion 9d, the pressing portion 4C is elastically deformed such that the slit 16 is contracted. When the insertion convex portion 11C is further inserted into the communication path 9 from the opening portion 9d, the protrusion 12a is inserted into the first lumen 5B by a resilience of the pressing portion 4C. Here, the suture thread 100 is pushed to the inner wall of the first lumen 5B by the protrusion 12a.

Even in this constitution, the same effect as the above-mentioned third embodiment is exhibited.

In addition, the thread-fixing tool 1C can be easily assembled and the suture thread 100 can be securely fixed.

Further, since the pressing portion 4C has elasticity, the suture thread 100 can be pushed against the inner wall of the first lumen 5B with a constant pressing force regardless of a thickness of the suture thread 100. For this reason, a range of a thickness and hardness of the suture thread 100 that can be used by one kind of thread-fixing tool 1 is wide, and use convenience is improved.

(Fifth Embodiment)

A thread-fixing tool according to a fifth embodiment of the present invention will be described.

Figure 31:
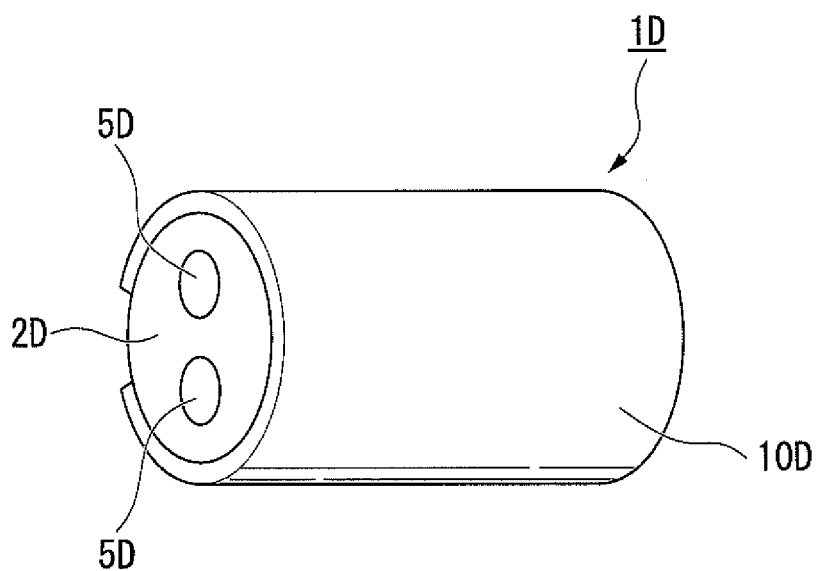
FIG. 31 is a perspective view showing a thread-fixing tool according to a fifth embodiment of the present invention.
Figure 32:
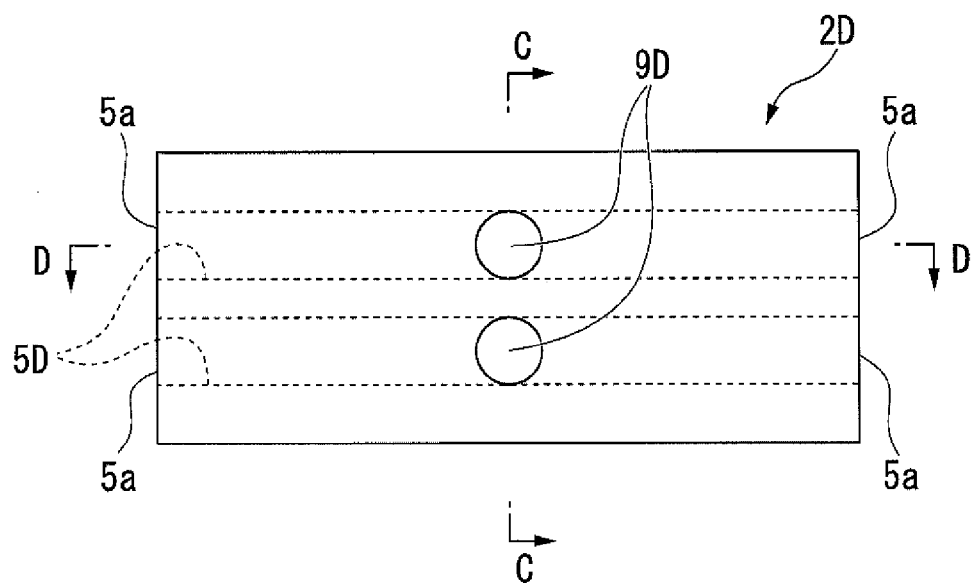
FIG. 32 is a side view showing a first member of the thread-fixing tool according to the fifth embodiment of the present invention.
Figure 33:
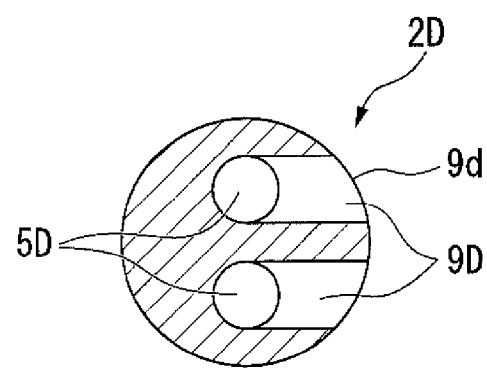
FIG. 33 is a cross-sectional view taken along line C-C of FIG. 32.

First, a constitution of a thread-fixing tool 1D according to the embodiment will be described with reference to FIGS. 31 to 35. FIG. 31 is a perspective view showing the thread-fixing tool 1D according to the embodiment. FIG. 32 is a side view showing a first member of the thread-fixing tool 1D. FIG. 33 is a cross-sectional view taken along line C-C of FIG. 32. FIG.

Figure 34:
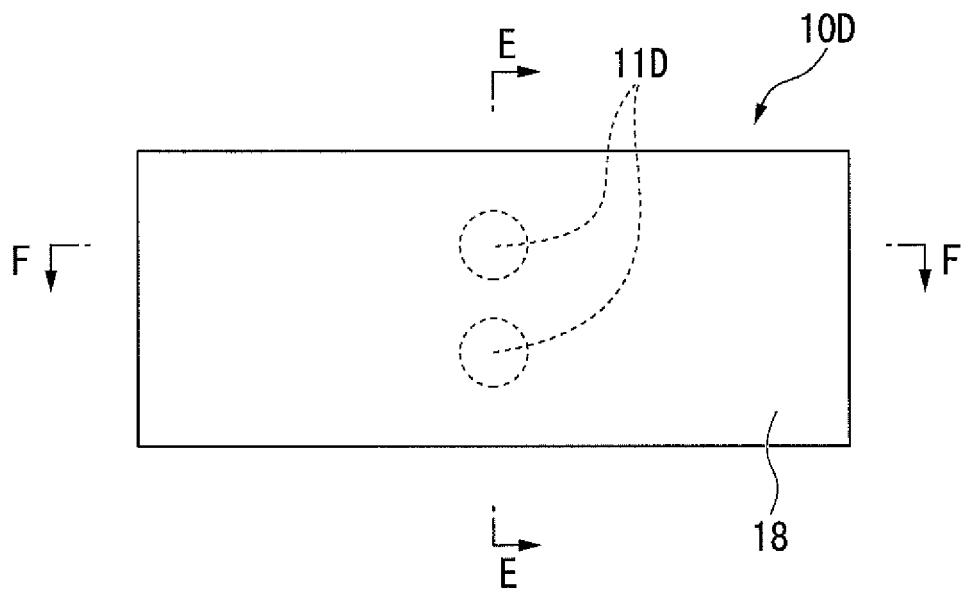
FIG. 34 is a side view showing a second member of the thread-fixing tool according to the fifth embodiment of the present invention.
Figure 35:
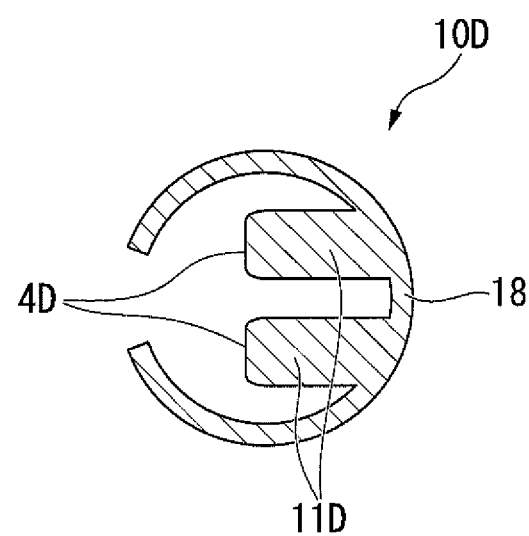
FIG. 35 is a cross-sectional view taken along line E-E of FIG. 34.

34 is a side view showing a second member 10D of the thread-fixing tool 1D. FIG. 35 is a cross-sectional view taken along line E-E of FIG. 34.

As shown in FIGS. 31 to 35, the thread-fixing tool 1D according to the embodiment includes a first member 2D having first lumens 5D and a communication path 9D, and includes a second member 10D having an insertion convex portion 11D and a connecting cover 18.

The first member 2D has a circular columnar shape having a cross-sectional shape perpendicular to the central axis. The two first lumens 5D are formed in the first member 2D. The first lumens 5D according to the embodiment are through-holes having first opening portions 5a formed in both end surfaces in the central axial direction of the first member 2D. Like the first lumen 5 described in the first embodiment, the suture threads 100 (see FIG. 36) are inserted into the first lumens 5D.

In the communication path 9D, the opening portion 9d through which the insertion convex portion 11D is inserted is formed in an outer circumferential surface of the first member 2D, and comes in communication with the first lumen 5D in the first member 2D. The communication path 9D extends in a direction perpendicular to the central axis of the first lumen 5D.

The insertion convex portion 11D formed at the second member 10D is inserted into the communication path 9D and a distal end thereof is disposed in the first lumen 5D. The distal end of the insertion convex portion 11D constitutes the pressing portion 4D to press the suture thread 100. In the embodiment, a distal surface of the insertion convex portion 11D is curved along a shape of the inner wall of the first lumen 5D. The number of insertion convex portions 11D is the same as that of the communication paths 9.

The connecting cover 18 is fixed to the insertion convex portion 11D instead of the flange portion 14 described in the first embodiment. The connecting cover 18 is a substantially tubular elastic member including an inner circumferential surface having a shape along the outer circumferential surface of the first member 2D. In the connecting cover 18, a portion of a tubular wall has a shape perforated in the central axial direction of the connecting cover 18, and the first member 2 is inserted into the connecting cover 18 as a portion at which the tubular wall of the connecting cover 18 is perforated is flared.

Figure 36:
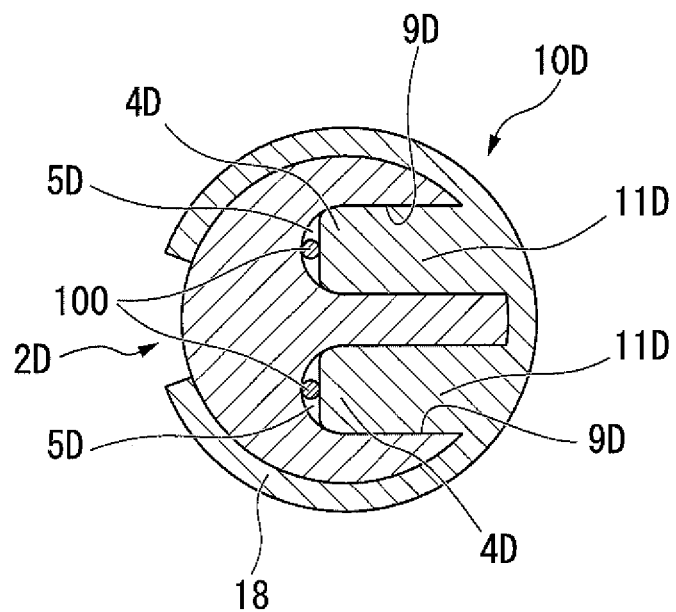
FIG. 36 is a cross-sectional view for describing an action of the thread-fixing tool according to the fifth embodiment of the present invention.

Next, an action of the thread-fixing tool according to the embodiment will be described. FIG. 36 is a cross-sectional view for describing the action of the thread-fixing tool.

During use of the thread-fixing tool 1D according to the embodiment, first, the suture threads 100 are inserted through the first lumens 5D one by one. After that, a forceps or the like is used to attach the connecting cover 18 to the first member 2D. Then, the insertion convex portion 11D of the second member 10D is inserted into the communication path 9D formed in the first member 2D, and the suture thread 100 is pushed against the inner wall of the first lumen 5D by the pressing portion 4D formed at the distal end of the insertion convex portion 11D. Accordingly, the suture thread 100 is fixed.

Like the thread-fixing tools 1, 1A, 1B and 1C of the above-mentioned first to fourth embodiments, the thread-fixing tool 1D according to the embodiment also presses the suture thread 100 in a direction perpendicular to the insertion direction of the suture thread 100. For this reason, the suture thread 100 can be fixed with a sufficient fixing force without applying a force in a direction in which the suture thread 100 is broken.

MODIFIED EXAMPLE 5-1

Figure 37:
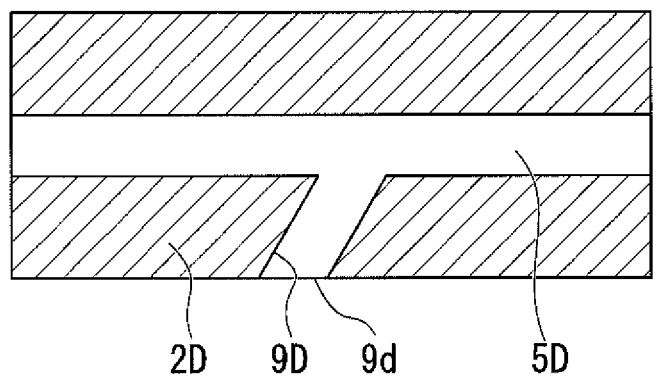
FIG. 37 is a cross-sectional view taken along line D-D of FIG. 32, showing a constitution according to a modified example of the fifth embodiment of the present invention.
Figure 38:
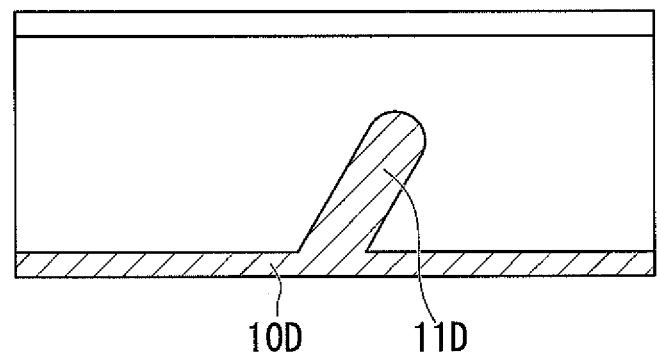
FIG. 38 is a cross-sectional view taken along line F-F of FIG. 34, showing a constitution according to the modified example of the fifth embodiment of the present invention.

Next, a modified example of the fifth embodiment will be described. FIG. 37 is a cross-sectional view taken along line D-D of FIG. 32, showing a constitution of the first member 2D according to the modified example. FIG. 38 is a cross-sectional view taken along line F-F of FIG. 34, showing a constitution of the second member 10D according to the modified example.

As shown in FIGS. 37 and 38, in the modified example, a shape of the communication path 9D formed in the first member 2D is different.

In the communication path 9D, an opening portion 9d into which the insertion convex portion 11D is inserted is formed in the outer circumferential surface of the first member 2D, and comes in communication with the first lumen 5D in the first member 2D. The communication path 9D extends in a direction crossing the central axis of the first lumen 5D.

In addition, the insertion convex portion 11D extends in a direction corresponding to the direction in which the communication path 9D extends, and is formed at the connecting cover 18.

For example, when the thread-fixing tool 1D of the modified example is used in a state in which the first member 2D is disposed such that the communication path 9D is inclined toward the biological tissue T from the opening portion 9d toward the first lumen 5D (in a state in which the biological tissue T is disposed at a right side of FIG. 37), the suture thread 100 is slightly pressed toward the biological tissue T by the insertion convex portion 11D, and binding of the biological tissue T is slightly attenuated. On the other hand, when the thread-fixing tool 1D is used in a state in which the first member 2D is disposed such that the communication path 9D is inclined to be spaced apart from the biological tissue as it goes from the opening portion 9d toward the first lumen 5D (in a state in which the biological tissue T is disposed at a left side of FIG. 27), the suture thread 100 is slightly pressed to be spaced apart from the biological tissue T by the insertion convex portion 11D, and binding of the biological tissue T is tightened.

In this way, in the modified example, a binding amount of the biological tissue T is adjusted when the second member 10D is attached to the first member 2D.

(Sixth Embodiment)

A thread-fixing tool according to a sixth embodiment of the present invention will be described.

Figure 39:
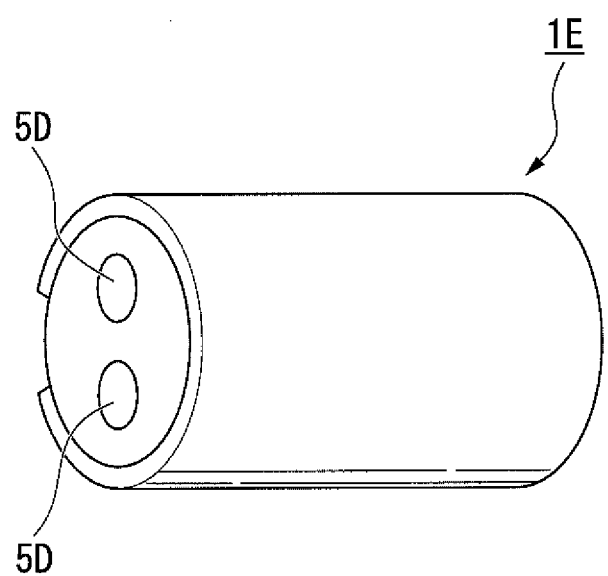
FIG. 39 is a perspective view showing a thread-fixing tool according to a sixth embodiment of the present invention.
Figure 40:
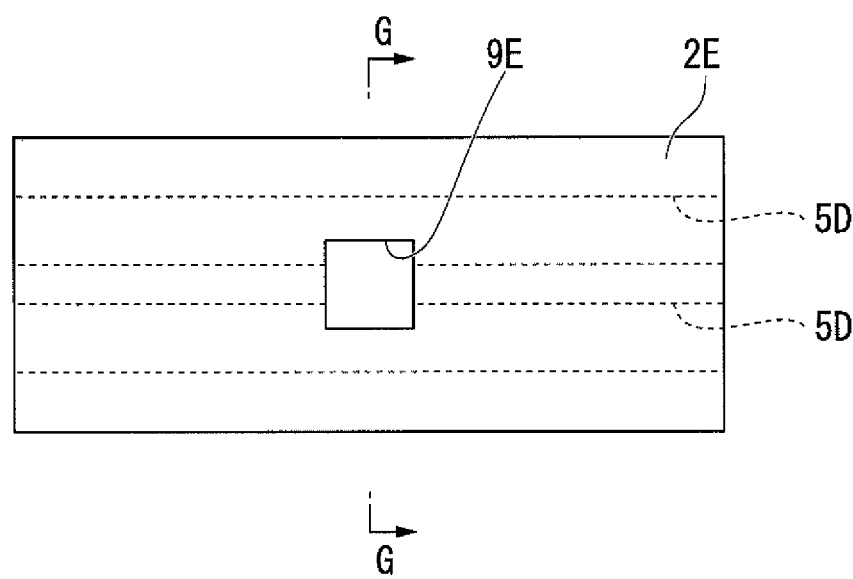
FIG. 40 is a side view showing a first member of the thread-fixing tool according to the sixth embodiment of the present invention.
Figure 41:
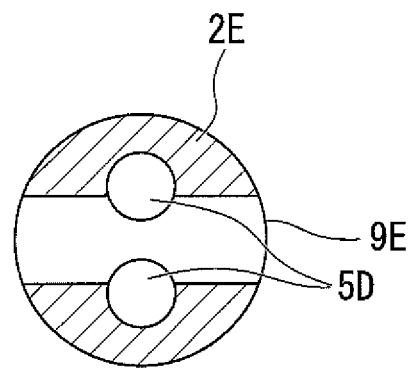
FIG. 41 is a cross-sectional view taken along line G-G of FIG. 40.
Figure 42:
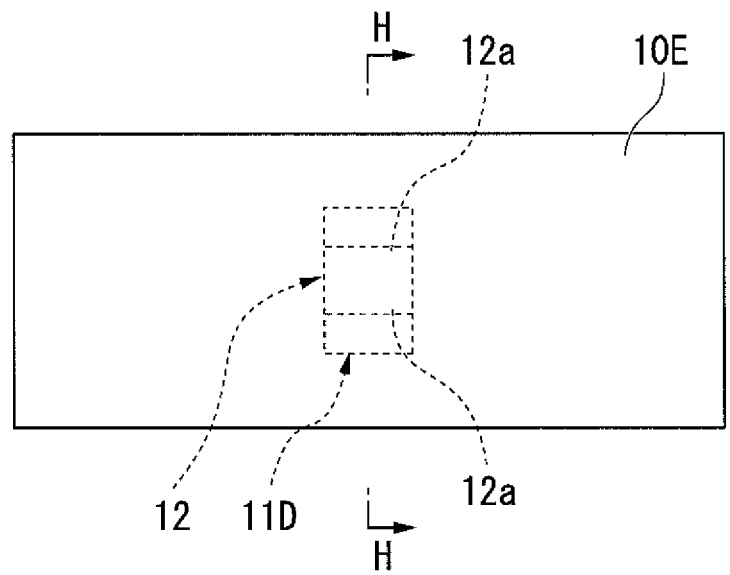
FIG. 42 is a side view showing a second member of the thread-fixing tool according to the sixth embodiment of the present invention.
Figure 43:
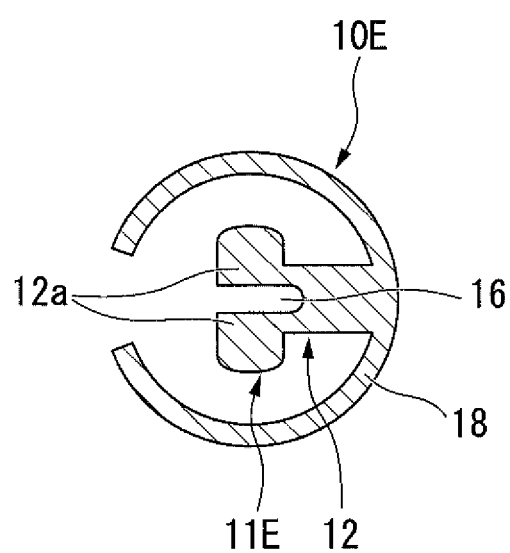
FIG. 43 is a cross-sectional view taken along line H-H of FIG. 42.

FIG. 39 is a perspective view showing a thread-fixing tool 1E according to the embodiment. FIG. 40 is a side view showing a first member 2E of the thread-fixing tool 1E according to the embodiment. FIG. 41 is a cross-sectional view taken along line G-G of FIG. 40. FIG. 42 is a side view showing a second member 10E of the thread-fixing tool 1E according to the embodiment. FIG. 43 is a cross-sectional view taken along line H-H of FIG. 42.

As shown in FIGS. 39 to 42, in the thread-fixing tool 1E of the embodiment, the first member 2E and the second member 10E have different constitutions from the fifth embodiment. The first member 2E has a different constitution from the fifth embodiment in that one communication path 9E in communication with both of the two first lumens 5D is provided. The second member 10E has an insertion convex portion 11E having a different constitution from the insertion convex portion 11D according to the fifth embodiment.

The communication path 9E extends in a direction perpendicular to the central axis of the first lumen 5D. The communication path 9E has an opening portion 9d formed in the outer circumferential surface of the first member 2E and into which the insertion convex portion 11E is inserted, and comes in communication with the first lumen 5D. In the communication path 9E, a cross-sectional shape perpendicular to the central axis of the communication path 9E is a rectangular shape.

In the insertion convex portion 11E formed at the second member 10E, a cross-sectional shape perpendicular to the central axis is a rectangular shape corresponding to the cross-sectional shape of the communication path 9. In addition, a distal end of the insertion convex portion 11E has a pressing portion 4E including the same constitution as the protrusion 12a and the slit 16 described in the fourth embodiment.

Figure 44:
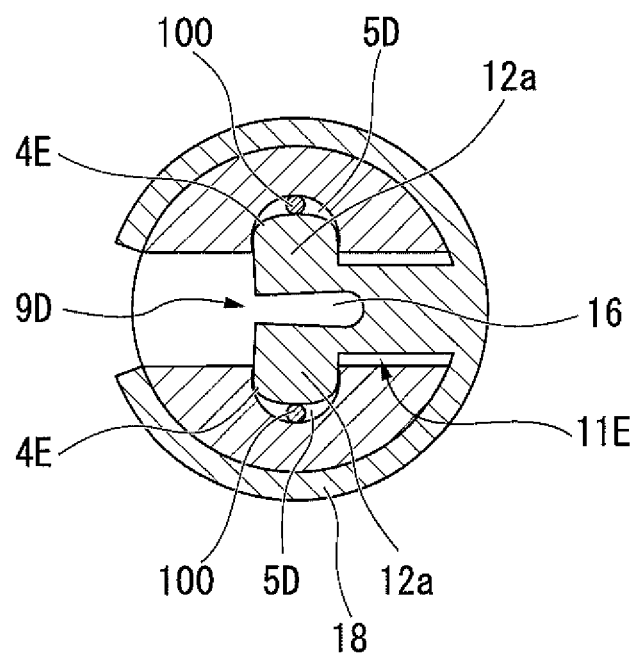
FIG. 44 is a cross-sectional view for describing an action of the thread-fixing tool according to the sixth embodiment of the present invention.

An action of the thread-fixing tool 1E according to the embodiment will be described. FIG. 44 is a cross-sectional view for describing the action of the thread-fixing tool.

In the embodiment, the insertion convex portion 11E inserted into the communication path 9E through the opening portion 9d is held in the communication path 9E in a state in which the pressing portion 4E is inserted into the first lumen 5D by the resilience of the pressing portion 4E. Accordingly, the suture threads 100 inserted into the first lumens 5D are pressed in a direction perpendicular to the insertion direction of the suture thread 100 by the pressing portion 4E.

In addition, like the fifth embodiment, in the embodiment, the connecting cover 18 is fitted onto the outer circumferential surface of the first member 2E, and the second member 10E is configured not to be easily removed from the first member 2E.

Further, in the embodiment, the pressing portion 4E is locked to the first lumen 5D having elasticity, and further, the connecting cover 18 is fitted onto the outer circumferential surface of the first member 2E. Accordingly, the second member 10E has a dual structure configured to prevent removal of the second member 10E from the first member 2E.

Hereinabove, while examples of the present invention have been described, the present invention is not limited to these examples. Additions, omissions, substitutions and other modifications of constitutions may be made without departing from the spirit of the present invention.

For example, the thread-fixing tool includes a columnar member having a columnar shape and a substantially tubular cover having a C-shaped cross-section perpendicular to the central axis of the inner surface along the outer circumferential surface of the columnar member and elasticity, and can fix the suture thread by sandwiching the suture thread between the first member and the cover.

In addition, for example, the thread-fixing tool may include a tubular member having a flexible tubular shape and into which a suture thread is inserted, a substantially tubular cover having an inner circumferential surface formed along an outer surface of the tubular member and a C-shaped cross-section perpendicular to a central axis thereof, and a protrusion formed at the inner circumferential surface of the cover and protruding inwardly from the inner circumferential surface of the cover, wherein, as the cover is attached to the tubular member, the tubular member is elastically deformed by the protrusion to close an inner lumen of the tubular member, and a suture thread inserted into the tubular member is pushed against and fixed to an inner wall of the tubular member.

What is claimed is:

1. A thread-fixing tool configured to fix a suture thread passing through a biological tissue, comprising:
a first member which has (i) a lumen disposed along a longitudinal axis of the first member and (ii) a communication path disposed along the longitudinal axis of the first member, the lumen being configured to receive the suture thread and the communication path communicating with an intermediate portion of the lumen; and
a second member which has (i) a shaft portion configured to be inserted into the communication path of the first member and (ii) a pressing portion formed at a distal portion of the shaft portion and which is capable of deforming outwardly in a radial direction of the shaft portion,
wherein a longitudinal axis of the lumen and a longitudinal axis of the communication path extend parallel with each other,
the longitudinal axis of the communication path and the longitudinal axis of the lumen are radially offset from each other in a radial direction of the lumen, and
the pressing portion is configured (i) to be guided to the communication path and to the intermediate portion of the lumen through the communication path and (ii) to be deformed in a direction crossing an insertion direction of the suture thread to push the suture thread against an inner wall of the lumen.

2. The thread-fixing tool according to claim 1, wherein the pressing portion is configured to be deformed in a direction perpendicular to the insertion direction of the suture thread so as to fix the suture thread in the lumen when the second member is inserted into the communication path.

3. The thread-fixing tool according to claim 1, wherein the pressing portion includes a protrusion having a restoring force that restores outwardly in the radial direction of the shaft portion, and
the pressing portion is configured to be inserted into the lumen such that the protrusion pushes the suture thread against the inner wall by a transformation of the protrusion from a state in which the protrusion is elastically deformed by a wall surface of the communication path and is inserted into the communication path to a state in which the protrusion is guided to the intermediate portion and is restored outwardly in the radial direction of the shaft portion.

4. The thread-fixing tool according to claim 1, wherein the first member includes a guide wall surface forming a part of the communication path to guide the pressing portion to the intermediate portion, the guide wall surface being configured to press the pressing portion in accordance with an insertion of the second member into the communication path, and
the pressing portion is configured to be inserted into the lumen and to push the suture thread against the inner wall of the lumen as the pressing portion is deformed and curved outwardly in the radial direction of the shaft portion by being pressed from the guide wall surface.

5. The thread-fixing tool according to claim 1, wherein:
the communication path is open at an end surface of the first member, and
the lumen is open at the end surface.

* * * * *